(12) United States Patent
Pulst

(10) Patent No.: US 7,585,629 B2
(45) Date of Patent: Sep. 8, 2009

(54) COMPOSITIONS AND METHODS FOR SPINOCEREBELLAR ATAXIA

(75) Inventor: Stefan M. Pulst, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 11/411,233

(22) Filed: Apr. 24, 2006

(65) Prior Publication Data

US 2006/0292604 A1 Dec. 28, 2006

Related U.S. Application Data

(60) Provisional application No. 60/674,182, filed on Apr. 22, 2005, provisional application No. 60/720,915, filed on Sep. 26, 2005.

(51) Int. Cl.
C07H 21/04 (2006.01)
C12Q 1/68 (2006.01)

(52) U.S. Cl. .......................... 435/6; 435/91.1; 435/91.2; 536/23.1; 536/24.3

(58) Field of Classification Search ....................... None
See application file for complete search history.

(56) References Cited

U.S. PATENT DOCUMENTS

2003/0092019 A1* 5/2003 Meyer et al. .................. 435/6

OTHER PUBLICATIONS

Guy et al. (Am. J. of Medial Genetics, vol. 88, pp. 57-60, 1999).*
Laurent et al. (Am. J. Of Medical Genetics, VOl. 116B, pp. 45-50, 2003).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Dror et al. (Mol. Psychiatry, vol. 4, pp. 254-260, 1999).*
Browne et al. (Nature Genetics , vol. 8, pp. 136-140, Oct. 1994).*
Aggarwal, S. K. et al., Contribution of the S4 segment to gating charge in the Shaker K+ channel. Neuron 16, 1169-1177 (1996).
Broman, K.W., et al., Comprehensive human genetic maps: individual and sex-specific variation in recombination. Am J Hum Genet 1998;63(3):861-9).
Chen, D.H., et al., The clinical and genetic spectrum of spinocerebellar ataxia 14. Neurology 2005;64:1258-1260.
Covarrubias, M., et al., express independent K+ current systems. Neuron 7, 763-773 (1991).
Delwart et al., Science 262:1257-1261 (1993).
Dib C, et al. A comprehensive genetic map of the human genome based on 5,264 microsatellites. Nature 1996;380(6570): 152-4.
Dudding T.E., et al. Autosomal dominant congenital non-progressive ataxia overlaps with the SCA15 locus. Neurology 2004;63:2288-2292.
Duprat, F., Susceptibility of cloned K+ channels to reactive oxygen species. Proc. Natl. Acad. Sci. U.S.A. 92, 11796-11800 (1995).
Dworakowska, B., et al., Acta Bioch. Pol. 47, 685 (2000).
Espinosa, F., et al. Alcohol hypersensitivity, increased locomotion, and spontaneous myoclonus in mice lacking the potassium channels Kv3.1 and Kv3.3. J. Neurosci. 21, 6657-6665 (2001).
Ghanshani, P., et al., Genomics 12, 190 (1992).
Goldman-Wohl, D.S., et al., N. Kv3.3b: a novel Shaw type potassium channel expressed in terminally differentiated cerebellar Purkinje cells and deep cerebellar nuclei. J. Neurosci. 14, 511-522 (1994).
Gomez C.M., Subramony SH. Dominantly inherited ataxias. Semin Pediatr Neurol 2003;10(3):210-212.).
Graves, T. D., et al., Neurological channelopathies. Postgrad. Med. J. 81, 20-32 (2005).
Hayashi, PCR Methods Applic. 1:34-38 (1991).
Herman-Bert A, et al. Mapping of spinocerebellar ataxia 13 to chromosome 19q13.3-q13.4 in a family with autosomal dominant cerebellar ataxia and mental retardation. Am J Hum Genet 2000;67:229-235 (2000).
Kruglyak L, et al., Parametric and nonparametric linkage analysis: a unified multipoint approach. Am J Hum Genet 1996;58:1347-1363.
Kruglyak L, et al., Faster multipoint linkage analysis using Fourier transformations, J Comput Biol 1998;5:1-7.
Lieberman A.P., et al., Triplet repeat expansion in neuromuscular disease. Muscle Nerve 2000;23(6):843-50.
Long, S.B., et al., Crystal structure of a mammalian voltage-dependent Shaker family K+ channel. Science 309, 897-890 (2005).
Mantuano E, et al., Spinocerebellar ataxia type 6 and episodic ataxia type 2: differences and similarities between two allelic disorders. Cytogenet Genome Res 2003;100(1-4):147-153.
Martina, M., et al., Properties and functional role of voltage-dependent potassium channels in dendrites of rat cerebellar Purkinje neurons. J. Neurosci. 23, 5698-5707 (2003).

(Continued)

Primary Examiner—Jeanine A Goldberg
(74) Attorney, Agent, or Firm—Hamilton, Brook, Smith & Reynolds, P.C.

(57) ABSTRACT

The autosomal dominant spinocerebellar ataxias (SCAs) represent a growing and heterogeneous clinical phenotype with ongoing discovery of causative etiologies. Methods: The authors collected DNA and clinically characterized a three-generation Filipino family segregating a dominant ataxia. Following elimination of several known SCA loci, a genome-wide linkage study was undertaken with additional fine mapping of 19q13. Results: Clinical characterization of affected family members revealed cerebellar signs including gait ataxia, limb ataxia/dysmetria, titubation, hypotonia, dysarthria, and nystagmus. Linkage was found in a ~4 cM region of 19q13 bounded by markers D19S867 and D19S553, with a maximum LOD score of 3.89 at markers D19S904, D19S246, and D19S907. This region overlaps with, though markedly reduces the previously described SCA13 locus. Conclusion: An autosomal dominant cerebellar ataxia clinically distinguishable from SCA13 overlaps with the SCA13 locus on chromosome 19q13.3.

4 Claims, 9 Drawing Sheets

OTHER PUBLICATIONS

Matsuura T, et al., Large expansion of the ATTCT pentanucleotide repeat in spinocerebellar ataxia type 10. Nat Genet 2000;26(2):191-194.

McKay, B.E., et al. ,Kv3 K+ channels enable burst output in rat cerebellar Purkinje cells. Eur. J. Neurosci. 20, 729-739 (2004).

McKay, B.E., et al., Physiological and morphological development of the rat cerebellar Purkinje cell. J. Physiol. epub ahead of print (2005).

Michalik A, et al., (2003) Pathogenesis of polyglutamine disorders: aggregation revisited. Hum Mol Genet 2003;12(2):173-186.).

Mulley, J.C., et al., Curr. Opin. Neurol. 16,171 (2003).

Mullis et al. (Eds.), The Polymerase Chain Reaction, Birkhauser, Boston, (1994).

Pulst, S.M., Ed. Genetics of Movement Disorders. Academic Press, San Diego 2002.

Pulst, S.M., Neurogenetics: single gene disorders. J Neurol Neurosurg Psych 2003;74:1608-1614.

Rae, L., et al., Exp. Eye. Res. 70,339 (2000).

Ranum L.P., et al., Myotonic dystrophy: RNA pathogenesis comes into focus. Am J Hum Genet 2004;74(5):793-804.

Raskind, W.H., et al., Familial spastic paraparesis: evaluation of locus heterogeneity, anticipation, and haplotype mapping of the SPG4 locus on the short arm of chromosome 2. Am J Med Genet 1997:74(1):26-36.

Rudy, B. et al., Kv3 channels: voltage-gated K+ channels designed for high-frequency repetitive firing. Trends Neurosci. 9, 517-526 (2001).

Ruppersberg, J.P. et al. Regulation of fast inactivation of cloned mammalian IK(A) channels by cysteine oxidation. Nature 352, 711-714 (1991).

Schöls L, et al., Autosomal dominant cerebellar ataxias: clinical features, genetics, and pathogenesis. Lancet Neurol 2004;(5):291-304.

Schulteis, C.T., et al., J. Biol. Chem. 273, 26210 (1998).

Seoh, S.A., et al., F. Voltage-sensing residues in the S2 and S4 segments of the Shaker K+ channel. Neuron 16, 1159-1167(1996).

Sheffield et al., "Identifying DNA Polymorphisms by Denaturing Gradient Gel Electrophoresis" in Innis et al., supra, 20 1990).

Shen, N. V. et al., Molecular recognition and assembly sequences involved in the subfamily-specific assembly of voltage-gated K+ channel subunit proteins. Neuron 14, 625-633 (1995).

Shieh, C.C., et al., Role of transmembrane segment S5 on gating of voltage-dependent K+ channels. J. Gen. Physiol. 109, 767-778 (1997).

Silverman, W.R., et al., Mg (2+) modulates voltage-dependent activation in ether-a-go-go potassium channels by binding between transmembrane segments S2 and S3. J. Gen. Physiol. 116, 663-677 (2000).

Smith-Maxwell, C.J., et al., Uncharged S4 residues and cooperativity in voltage-dependent potassium channel activation. J. Gen. Physiol. 111, 421-439 (1998).

Stevanin G, et al. Mutation in the catalytic domain of the protein kinase C γ and extension of the phenotype associated with spinocerebellar ataxia type 14. Arch Neurol 2004;61:1242-1248.

Trottier Y, et al., Polyglutamine expansion as a pathological epitope in Huntington's disease and four dominant cerebellar ataxias. Nature 1995;378:403-406.

Vega-Saenz de Miera, E., et al. (1992) Biochem Biophys Res Comm 186, 1681-1687.

Waters, M.F., et al. Neurology epub ahead of print (2005).

Weiser, M. et al. Differential expression of Shaw-related K+ channels in the rat central nervous system. J. Neurosci. 14, 949-972 (1994).

White et al., Genomics 12:301-306 (1992).

Winter et al., Proc. Natl. Acad. Sci. 82:7575-7579 (1985).

Zander C, et al., Multivariate analysis of factors influencing repeat expansion detection. Genome Res 1998;8:1085-1094.

Zu L, et al., Mapping of a new autosomal dominant spinocerebellar ataxia to chromosome 22. Am J Hum Genet 1999;64(2):594-599.

Waters, M.F., et al., "Mutations in Voltage-Gated Potassium Channel KCNC3 Cause Degenerative and Developmental Central Nervous System Phenotypes," *Nature Genetics*, 38(4): 447-451 (2006).

\* cited by examiner

| Individual | I-1 | II-1 | II-4 | II-5 | II-6 | II-7 | II-10 | II-14 | III-2 | III-3 |
|---|---|---|---|---|---|---|---|---|---|---|
| Gait ataxia | +++ | +++ | ++ | ++ | + | + | + | + | + | + |
| Limb ataxia | +++ | +++ | | + | + | | | + | + | + |
| Titubation | ++ | | | + | | | | | | |
| Hypotonia | ++ | ++ | | | | | | + | ++ | |
| Dysarthria | ++ | ++ | | + | | | | + | + | + |
| Nystagmus | | | | + | | | | | | |
| Hyperreflexia | | | | ++ | | | | + | | |

FIGURE 3

```
KCNC1       1  ------------------------------------------------
KCNC2       1  ------------------------------------------------
KCNC3       1  MLSSVCVSSFRGRQGASKQQPAPPPQPPESPPPPPLPPQQQQPAQPGPAA
KCNC4       1  MISSVCVSSYRGRKSGNKP-----------------------------
consensus   1  .............   ..

KCNC1       1  -----------------------MGQ----GDESERIVINVGGTRHQ
KCNC2       1  -----------------------MGK----IENNERVILNVGGTRHE
KCNC3      51  SPAGPPAPRGPGDRRAEPCPGLPAAAMGRHGGGGGDSGKIVINVGGVRHE
KCNC4      20  ----------------PSKTCLKEEMAK----GEASEKIIINVGGTRHE
consensus  51                         *..           ****.**.

KCNC1      21  TYRSTLRTLPGTRLAWLA-------------------------------
KCNC2      21  TYRSTLKTLPGTRLALLASSEPPGDCLTTAGDKLQPSPPPLSPPPRAPPL
KCNC3     101  TYRSTLRTLPGTRLAGLT-------------------------------
KCNC4      49  TYRSTLRTLPGTRLAWLA-------------------------------
consensus 101  ******.********.*.

KCNC1      39  EPDAHSHF--------------DYDPRADEFFFDRHPGVFAHILNYYRT
KCNC2      71  SPGPGGCFEGGAGNCSSRGGRASDHPGGGREFFFDRHPGVFAYVLNYYRT
KCNC3     119  EPEAAARF--------------DYDPGADEFFFDRHPGVFAYVLNYYRT
KCNC4      67  DPDGGGRPETDGGGVGSSG----SSGGGGCEFFFDRHPGVFAYVLNYYRT
consensus 151  .*......   ..    ..    ...   ...************..******

KCNC1      74  GKLHCPADVCGPLYEEELAFWGIDETDVEPCCWMTYRQHRDAEEALDSFG
KCNC2     121  GKLHCPADVCGPLFEEELAFWGIDETDVEPCCWMTYRQHRDAEEALDIFE
KCNC3     154  GKLHCPADVCGPLFEEELGFWGIDETDVEACCWMTYRQHRDAEEALDSFE
KCNC4     113  GKLHCPADVCGPLFEEELTFWGIDETDVEPCCWMTYRQHRDAEEALDIFE
consensus 201  *************.*****.********.*****************.*.

KCNC1     124  GAPLDNSADDADADGPGD------SGDGEDELEMT----KRLALSDS---
KCNC2     171  TPDLIG-----------------GDPGDDEDLA---AKRLGIEDA-AG
KCNC3     204  APDPAGAANAANAAGAHDGGLDDEAGAGGGGLDGAGGELKRLCFQDAGGG
KCNC4     163  SPDGGG-----SGAGPSD-------EAGDDERELA---LQRLGPHEGGAG
consensus 251  .....  .  ....  .            .........  ..**..  ......

KCNC1     161  ---PDGRPGG----FWRRWQPRIWALFEDPYSSRYARYVAFASLFFILVS
KCNC2     198  LGGPDGKSGR-----WRRLQPRMWALFEDPYSSRAARFIAFASLFFILVS
KCNC3     254  AGGPPGGAGGAGGTWWRRWQPRVWALFEDPYSSRAARYVAFASLFFILIS
KCNC4     198  HGAGSGGC-------RGWQPRMWALFEDPYSSRAARVVAFASLFFILVS
consensus 301  ....*.. ..    ..*..***.*********.**..*********.*

KCNC1     204  ITTFCLETHERFNPIVNKTEIE------NVRNGTQVRYYREAETEAFLT
KCNC2     243  ITTFCLETHEAFNIVKNKTE--------PVINGTSVVLQYEIETDPALT
KCNC3     304  ITTFCLETHEGFIHISNKTVTQASPIPGAPPENITNV----EVETEPFLT
KCNC4     240  ITTFCLETHEAFNIDRNVTEIL-------RVGNITSVHFRREVETEPILT
consensus 351  **********.*.....*.*..         .. * *.*.. .*.**...**

KCNC1     247  YIEGVCVVWFTFEFLMRVIFCPNKVEFIKNSLNIIDFVAILPFYLEVGLS
KCNC2     284  YVEGVCVVWFTFEFLVRIVFSPNKLEFIKNLLNIIDFVAILPFYLEVGLS
KCNC3     350  YVEGVCVVWFTFEFLMRITFCPDKVEFLKSSLNIIDCVAILPFYLEVGLS
KCNC4     283  YIEGVCVLWFTLEFLVRIVCCPDTLDFVKNLLNIIDFVAILPFYLEVGLS
consensus 401  *.*****.***.***.*.....*. ...*.*. *****.*******************
```

FIGURE 8

```
KCNC1      297  GLSSKAAKDVLGFLRVVRFVRILRIFKLTRHFVGLRVLGHTLRASTNEFL
KCNC2      334  GLSSKAAKDVLGFLRVVRFVRILRIFKLTRHFVGLRVLGHTLRASTNEFL
KCNC3      400  GLSSKAAKDVLGFLRVVRFVRILRIFKLTRHFVGLRVLGHTLRASTNEFL
KCNC4      333  GLSSKAARDVLGFLRVVRFVRILRIFKLTRHFVGLRVLGHTLRASTNEFL
consensus  451  ******.*******************************************

KCNC1      347  LLIIFLALGVLIFATMIYYAERIGAQPNDPSASEHTHFKNIPIGFWWAVV
KCNC2      384  LLIIFLALGVLIFATMIYYAERVGAQPNDPSASEHTQFKNIPIGFWWAVV
KCNC3      450  LLIIFLALGVLIFATMIYYAERIGADPDDILGSNHTYFKNIPIGFWWAVV
KCNC4      383  LLIIFLALGVLIFATMIYYAERIGARPSDPRGNDHTDFKNIPIGFWWAVV
consensus  501  *********************.**.*.*.....**.*************

KCNC1      397  TMTTLGYGDMYPQTWSGMLVGALCALAGVLTIAMPVPVIVNNFGMYYSLA
KCNC2      434  TMTTLGYGDMYPQTWSGMLVGALCALAGVLTIAMPVPVIVNNFGMYYSLA
KCNC3      500  TMTTLGYGDMYPKTWSGMLVGALCALAGVLTIAMPVPVIVNNFGMYYSLA
KCNC4      433  TMTTLGYGDMYPKTWSGMLVGALCALAGVLTIAMPVPVIVNNFGMYYSLA
consensus  551  *********** **************************************

KCNC1      447  MAKQKLPKKKKKHIPRPPQLGSPNYCKSV----------------------
KCNC2      484  MAKQKLPRKRKKHIPPAPQASSPTFCKTE----------------------
KCNC3      550  MAKQKLPKKKNKHIPRPPQPGSPNYCKPDPPPPPPPHPHHGSGGISPPPP
KCNC4      483  MAKQKLPKKRKKHVPRPAQLESPMYCKSE----------------------
consensus  601  ******.*..**.*....*..**..**..

KCNC1      476  ------------------------------VNSPHHSTQSDTCPLA
KCNC2      513  ------------------------------LNMACNSTQSDTCLGK
KCNC3      600  ITPPSMGVTVAGAYPAGPHTHPGLLRGGAGGLGIMGLPPLPAPGEPCPLA
KCNC4      512  ------------------------------ETSPRDSTCSDTSPPA
consensus  651                                .....  ..........

KCNC1      492  QEE-ILEINRA-------------------------------GRKPLRG
KCNC2      529  DNR-LLEHNRS-----------VLSGDDSTGSEPPL----SPPERLPIRR
KCNC3      650  QEE-VIEINRADPRPNGDPAAAALAHEDCPAIDQPAM---SPEDKSPITP
KCNC4      528  REEGMIERKRADSKQNGD-ANAVLSDEEGAGLTQPLASSPTPEERRALRR
consensus  701  ... ..*...*...  ... .  .....  .....    ........

KCNC1      509  MSI-------------------------------------------
KCNC2      563  SSTRDKNRRGETCFLLTTGDYTCASDGGIRKGYEKSRSLNNIAGLAGNAL
KCNC3      696  GS-RGRYSRDRACFLLT--DYAPSPDGSIRKATGAPPLPPQDWRKPGPPS
KCNC4      577  STTRDRNKKAAACFLLSTGDYACA-DGSVRKGTFVLRDL-----------
consensus  751  .........  ...........  ........  . ...  .

KCNC1           --------------------------------
KCNC2      613  RLSPVTSPYNSPCFLRRSRSPIPSIL
KCNC3      743  FLPDLNANAAAWISP----------
KCNC4      615  ---PLQHSPEAACPPTAGTLFLPH--
consensus  801  . ...    . ...          ..
```

FIGURE 8 CONTINUED

COMPOSITIONS AND METHODS FOR SPINOCEREBELLAR ATAXIA

This application claims priority to U.S. Patent Application Nos. 60/674,182, filed Apr. 22, 2005 and 60/720,915, filed Sep. 26, 2005.

GOVERNMENT INTEREST

This invention was made with United States Government support under Grants No. R01GM43459, R01GM66686, R01N533123 and T32GM065823, awarded by the National Institutes of Health. The United States Government has certain rights in this invention.

FIELD OF THE INVENTION

The present invention relates to the diagnosis and treatment of neurodevelopmental and neurodegenerative diseases.

BACKGROUND OF THE INVENTION

The dominant spinocerebellar ataxias (SCA) are a growing group of heterogeneous neurodegenerative diseases with phenotypes consisting of cerebellar ataxia with or without extrapyramidal signs, dysarthria, occulomotor abnormalities, upper and lower motor neuron signs, cognitive decline, epilepsy, autonomic dysfunction, sensory deficits, and psychiatric manifestations. (Pulst S M, ed. Genetics of Movement Disorders. Academic Press, San Diego 2002; Schöls L, Bauer P, Schmidt T, Schulte T, Riess O. Autosomal dominant cerebellar ataxias: clinical features, genetics, and pathogenesis. Lancet Neurol 2004; (5):291-304.) A total of twenty-six loci are known, and for ten SCAs the causative gene or mutation has been determined. The majority of these are represented by abnormal CAG repeat expansions.

Despite the remarkable progress in identifying loci and genes for the dominant ataxias, approximately 40% of SCAs remain unaccounted for. Clinical characterization of the dominant SCAs is difficult, given both the degree of intra- and interfamilial variability and phenotypic similarity seen in mutations of different genes. (Mantuano E, Veneziano L, Jodice C, Frontali M. Spinocerebellar ataxia type 6 and episodic ataxia type 2: differences and similarities between two allelic disorders. Cytogenet Genome Res 2003; 100(1-4): 147-153; Gomez C M, Subramony S H. Dominantly inherited ataxias. Semin Pediatr Neurol 2003; 10(3):210-212.) Even for ataxias which share polyglutamine repeat expansions, in vivo and in vitro experiments have revealed remarkable differences in disease pathogenesis. (Ranum L P, Day J W. Myotonic dystrophy: RNA pathogenesis comes into focus. Am J Hum Genet 2004; 74(5):793-804; Lieberman A P, Fischbeck K H, Triplet repeat expansion in neuromuscular disease. Muscle Nerve 2000; 23(6):843-50; Michalik A, Van Broeckhoven C. (2003) Pathogenesis of polyglutamine disorders: aggregation revisited. Hum Mol Genet 2003; 12(2): 173-186.) The identification of mutations causing neurodevelopmental and neurodegenerative diseases and the elucidation of the molecular mechanisms by which they cause disease thus represents a major advance in the diagnosis and treatment of neurodegenerative and neurodevelopmental diseases.

BRIEF DESCRIPTION OF THE DRAWINGS

FIG. 3: Table 1: Clinical features in select affected family members (+—mild, ++—moderate, +++—severe).

FIG. 8: Sequence alignment of the KCNC family of voltage-gated potassium channels showing conservation of residues, including residues R420, R417 and F448 in KCNC3. The KCNC1 amino acid sequence is shown in SEQ ID NO: 15, the KCNC2 amino acid sequence is shown in SEQ ID NO: 16, the KCNC3 amino acid sequence is shown in SEQ ID NO: 17 and the KCNC4 amino acid sequence is shown in SEQ ID NO: 18.

DETAILED DESCRIPTION OF THE INVENTION

Figure 1:
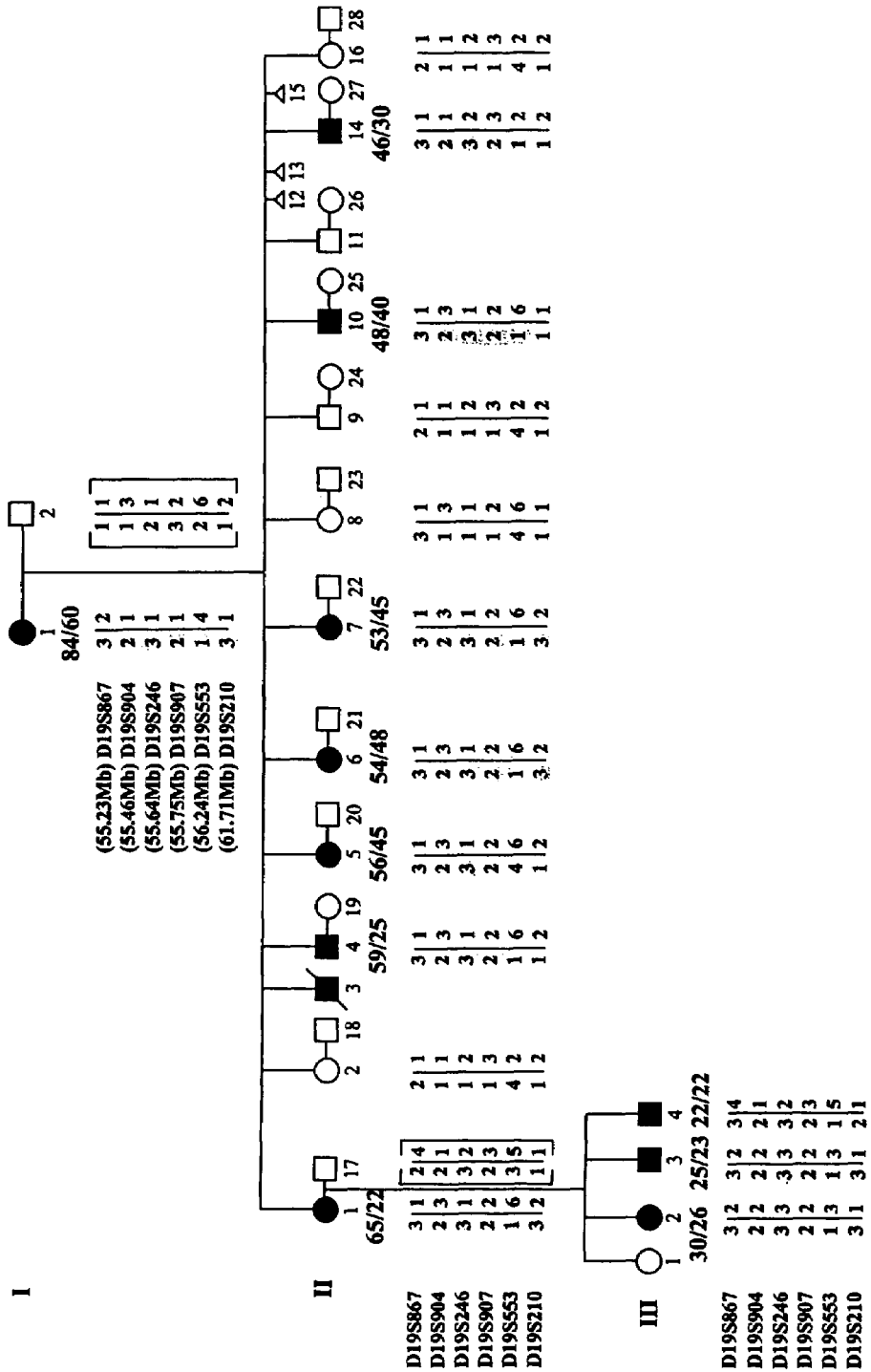
FIG. 1: Haplotypes for six informative chromosome 19 markers in the Filipino pedigree assuming the smallest number of recombination events. Note critical recombination events in individuals II-5 and II-8. Affected individuals are represented by darkened symbols. Age at examination and age-of-onset are shown in bold above the haplotype.

The present invention demonstrates for the first time that mutations in voltage-gated potassium channel can cause developmental and degenerative neurological diseases. After evaluating a family pedigree with adult-onset ataxia, the causative mutation for a spinocerebellar ataxia was mapped to chromosome 19, locus q13, overlapping the SCA13 locus described in a French pedigree with childhood-onset mental retardation, ataxia, and seizures. Sequencing the gene revealed KCNC3 (Kv3.3), a voltage-gated Shaw potassium channel with enriched cerebellar expression, carrying mutations 1554G→A (R420H) in Filipino, 1639C→A (F448L) in French pedigrees, and R417H. Wildtype KCNC3 channels expressed in *Xenopus* oocytes had the expected depolarized activation range and fast deactivation kinetics. KCNC3 R420H had no detectable channel activity when expressed alone, and strong dominant negative effects when co-expressed with wildtype. KCNC3 F448L altered gating such that activation was shifted ~13 mV toward the hyperpolarized direction, and channel closing was ~7-fold slower than wildtype. The R420H and F448L mutations are expected to change the output characteristics of fast spiking cerebellar neurons, where KCNC channels confer capacity for high frequency firing. Thus, the present invention provides for the identification of voltage-gated potassium channel mutations as a new class of genes involved in neurodegenerative diseases.

Because KCNC3 encodes a voltage-gated potassium channel belonging to the Shaw subfamily of K+ channels, it will now be possible to identify mutations in other voltage-gated potassium channels belonging to the same or related families of potassium channels, that are involved in neurodegenerative diseases. For example, the Shaker, Shab, Shaw, Shal families of voltage-gated potassium channels share significant homology throughout the functional domains that have been shown by the present invention to be involved in neurodevelopmental and neurodegenerative diseases. Thus, mutations in KCNA (Shaker): KCNA 1, 5 and 6 genes located in cluster on Chromosome 12p13, KCNA1 (Kv1.1), KCNA2 (Kv1.2), KCNA3 (Kv1.3), KCNA4 (Kv1.4), KCNA4L, KCNA5 (Kv1.5), KCNA6 (Kv1.6), KCNA7, KCNA8/KCNA9 (KCNQ1), KCNA10, KCNAB1 (Kv-β-1.1), KCNAB2 (Kv-β-1.2), KCNAB3, KCNB (Shab), KCNB1 (Kv2.1), KCNB2 (Kv2.2), KCNC (Shaw), KCNC1 (Kv3.1), KCNC2 (Kv3.2), KCNC3 (Kv3.3), KCNC4 (Kv3.4), KCND (Shal), KCND1 (Kv4.1), KCND2 (Kv4.2), KCND3 (Kv4.3) can now be detected and diagnosed in neurodevelopmental and neurodegenerative disease. All of the foregoing voltage-gated potassium channels are well known and their nucleotide and amino acid sequences are publicly available. In addition, as shown in FIG. 8, the KCNC channels 1-4 share significant sequence homology with each other, including a large number of highly conserved residues, such as R420, R417 and F448. In addition, some members of different voltage-gated potassium channel families interact with each other, as in heteromultimerization. For example, KCNC3 frequently heterodimerizes with other members of the KCNC family. Thus, mutations in functional domains of any of the closely related members of the KCNC family are predicted to produce phenotypes similar to those produced by the R420H, R417H, and F448L mutations characterized herein. Dominant spinocerebellar ataxias (SCA) are a group of heterogeneous neurodegenerative diseases with phenotypes consisting of cerebellar ataxia, extrapyramidal signs, dysarthria, oculomotor abnormalities, motor neuron signs, cognitive decline, epilepsy, autonomic dysfunction, sensory deficits, and psychiatric manifestations.

The present invention provides a method of diagnosing neurodegenerative and/or neurodevelopmental disease in an individual by detecting a disease-associated mutation linked to a voltage-gated potassium channel locus. The disease-associated mutation can be linked to but outside a gene coding for a voltage-gated potassium channel or can be within the gene, such as in a coding sequence, 5' or 3' regulatory region, or within an intronic sequence.

In the methods of the invention, the disease-associated mutation can produce, for example, a functionally compromised gene product, including a dominant negative gene product. Examples of neurodevelopmental and neurodegenerative disease-associated mutations occurring within a voltage-gated potassium channel nucleotide sequence include nucleotide variations at nucleotide 1554, and nucleotide 1639 of KCNC3, and analogous positions in related channels.

A variety of molecular methods useful in detecting a mutation in a voltage-gated potassium channel are well known in the art. For example, allele-specific oligonucleotide hybridization involves the use of a labeled oligonucleotide probe having a sequence perfectly complementary, for example, to a disease-associated sequence. Under appropriate conditions, the allele-specific probe hybridizes to a nucleic acid containing the disease-associated mutation but does not hybridize to the corresponding wild type nucleic acid sequence having one or more nucleotide mismatches. If desired, a second allele-specific oligonucleotide probe that matches the wild type sequence also can be used. Similarly, the technique of allele-specific oligonucleotide amplification can be used to selectively amplify, for example, a disease-associated polymorphic sequence by using an allele-specific oligonucleotide primer that is perfectly complementary to the nucleotide sequence of a disease-associated allele but which has one or more mismatches as compared to the corresponding wild type sequence (Mullis et al. (Eds.), The Polymerase Chain Reaction, Birkhauser, Boston, (1994), which is incorporated herein by reference).

A heteroduplex mobility assay (HMA) is another well known assay that can be used to diagnose a neurodegenerative and/or neurodevelopmental disease caused by a mutation in a voltage-gated potassium channel according to a method of the invention. HMA is useful for detecting the presence of a polymorphic sequence since a DNA duplex carrying a mismatch, such as a heteroduplex between a wild type and mutated DNA fragment, has reduced mobility in a polyacrylamide gel compared to the mobility of a perfectly base-paired duplex (Delwart et al., Science 262:1257-1261 (1993); White et al., Genomics 12:301-306 (1992), each of which is incorporated herein by reference). The technique of single strand conformation polymorphism (SSCP) also can be used to detect the presence of a mutation in a voltage-gated potassium channel (see Hayashi, PCR Methods Applic. 1:34-38 (1991), which is incorporated herein by reference). This technique can be used to detect mutations based on differences in the secondary structure of single-strand DNA that produce an altered electrophoretic mobility upon non-denaturing gel electrophoresis.

Denaturing gradient gel electrophoresis (DGGE) also can be used to detect a mutation in a voltage-gated potassium channel. In DGGE, double-stranded DNA is electrophoresed in a gel containing an increasing concentration of denaturant; double-stranded fragments made up of mismatched wild type and disease-associated sequences have segments that melt more rapidly, causing such fragments to migrate differently as compared to perfectly complementary sequences obtained from normal individuals (Sheffield et al., "Identifying DNA Polymorphisms by Denaturing Gradient Gel Electrophoresis" in Innis et al., supra, 20 1990).

Other well-known approaches for analyzing a mutation include automated sequencing, RNAase mismatch techniques (Winter et al., Proc. Natl. Acad. Sci. 82:7575-7579 (1985), which is incorporated herein by reference) and the use of restriction fragment length polymorphisms (see Innis et al., supra, 1990). For families in which the disease-associated mutation has been defined, automated sequencing of the region of interest can be particularly useful in diagnosing a neurodegenerative or neurodevelopmental disease. In addition, dot-blot hybridization, RFLP analysis and many more techniques well known in the art can be used for the purposes of the present invention.

A three-generation Filipino family segregating a dominant ataxia with prominent cerebellar signs and symptoms as well as cerebellar atrophy on MR imaging (FIGS. 1a & b) has been previously described. The clinical and imaging phenotypes were typical of degenerative SCAs. A genome-wide linkage scan revealed a disease locus in a ~4 cM region of 19q13, with a 3.89 LOD score. This region partially overlapped the SCA13 locus4, though the Filipino phenotype was clinically distinguishable from SCA13. For high-resolution mapping we generated novel dinucleotide markers from the Ensembl genome browser (release 31.35d). The linkage region was reduced to ~900K bases. Haplotypes for the novel markers are shown in FIG. 1a. Several markers including D19S904 showed no recombination events. Obligate recombinants were detected for both D19S867 and D19S553, which defined a physical candidate region with the LOD-1 drop interval providing a probable location of the disease gene near D19S904. This region contained approximately forty candidate genes, including KCNC3. Direct sequencing revealed two missense mutations in exon 2. The Filipino pedigree contained 1554G→A, encoding R420H in the third conserved arginine residue in S4 (FIG. 1c). The French pedigree contained 1639C→A, encoding F448L near the cytoplasmic end of S5 (FIG. 1d).

Among voltage-gated K+ channels, the functional properties of Kv3 channels are distinct. Kv3 channels activate in a more depolarized range and close much more rapidly compared to other Kv channels[5]. These properties facilitate high frequency firing of action potentials with little or no adaptation, a characteristic of neuronal populations found in the mammalian neocortex, hippocampus, auditory nuclei, and cerebellum[5]. Like other voltage-gated K+ channels, Kv3 channels are tetramers. Different Shaw family subunits are able to co-assemble with each other, but not with subunits from other Kv subfamilies[6,7]. Each subunit has six transmembrane segments and a re-entrant loop (FIG. 2a). The first four transmembrane segments, S1-S4, constitute the voltage sensor domain, whereas the last two segments, S5 and S6, and the re-entrant loop form the ion-selective pore[8]. The Filipino mutation is located in S4, the main voltage-sensing element and changes one of the multiple positively charged residues that respond to changes in membrane potential[9,10]. The French mutation is in the cytoplasmic end of S5, which is involved in coupling voltage-sensor conformational changes with opening and closing of the pore[11]. The depolarized voltage dependence and rapid deactivation that are characteristic of Kv3 channels are related properties conferred by specific amino acid residues in the voltage sensor and S5[11,12]. Importantly, KCNC3 protein sequences in S4 and S5 are 100% conserved amongst phyla, suggesting strong selection for the specialized role of these channels (FIG. 2b). Consistent with this observation, screening over four hundred alleles from normal individuals of Filipino or Anglo-European descent revealed no polymorphisms at either site.

To investigate the functional consequences of the SCA13 mutations, we expressed wildtype and mutant KCNC3 alleles in *Xenopus laevis* oocytes and recorded channel activity using a two electrode voltage clamp. Activation of the wild type Kv3.3 channel was detected at −10 mV and more positive potentials (FIG. 3a). Upon repolarization to −90 mV, the channel closed quickly. In contrast, expression of R420H resulted in no detectable channel activity (FIG. 3a). Co-expression of wildtype Kv3.3 and R420H subunits led to suppression of current amplitude consistent with a dominant negative effect (FIGS. 3b & c). R420H did not suppress the expression of Shaker, a member of the Kv1 family (FIG. 3c). These results indicated that Kv3 subfamily-specific co-assembly of wildtype and mutant subunits produced non-functional channels.

Expression of F448L produced channels with altered gating. Activation of F448L was detected at −20 mV, compared to −10 mV for wildtype (FIG. 4a). Analysis of the probability of opening as a function of voltage confirmed that activation was shifted ~13 mV toward the hyperpolarized direction (FIG. 4b). Activation kinetics of F448L and wildtype were similar at voltages where both have a maximal open probability (FIG. 4c). However, deactivation kinetics of F448L were dramatically slower. Tail currents were recorded after repolarization to −90 mV using an 89 mM Rb+bath solution, and fitted with a single exponential component (FIG. 4d). This revealed a ~7-fold slowing of channel closure in the F448L channel. The hyperpolarized shift in the probability of opening and the slower rate of deactivation are related findings indicating that F448L increases the relative stability of the open state. F448L makes the properties of Kv3.3 channels more similar to those of Shaker and other channels that normally have a leucine residue in the analogous position (FIG. 2b).

Although abnormalities of ion channels are rare causes of diseases of the heart, kidney, and skeletal muscle[13,14], KCNC3 was not a likely candidate for a degenerative ataxia, as potassium channel mutations are not associated with neurodegeneration, but with episodic phenomena such as epilepsy and episodic ataxia. Furthermore, KCNC3 deficiency in the mouse did not produce a phenotype[15].

Unlike other SCA genes implicated in neurodegeneration, the physiological functions of Kv3 channels in the cerebellum have been extensively studied and are reasonably well understood[16,17]. Kv3.3 is expressed in cerebellar granule cells, Purkinje cells, and deep cerebellar neurons, where it may form heteromultimeric channels by co-assembly with Kv3.1 and/or Kv3.4[18,19]. In Purkinje cells, Kv3 channels are involved in repolarizing both somatic Na+ spikes and dendritic Ca3+ spikes[17]. Kv3 channels are essential for fast spiking in neurons that fire hundreds of action potentials per second with little or no frequency adaptation[5]. Because of their depolarized activation range, Kv3 channels open only during action potentials, contribute to fast repolarization, and thus promote recovery of Na+ channels from inactivation. Fast deactivation of Kv3 channels limits the time course of the after-hyperpolarization, thereby shortening the refractory period.

In all likelihood, the SCA13 mutations disrupt the firing properties of fast spiking cerebellar neurons. Although the Kv3.3 knock-out mouse has no obvious motor phenotype, the double Kv3.1/Kv3.3 knock-out has dramatic symptoms, including tremor and severe ataxia[15]. Because R420H and R417H are expected to suppress the functional expression of Kv3.3 as well as other subunits in the Kv3 family, these mutations may be more comparable to the double knockout. Pharmacological suppression of Kv3 activity in cerebellar neurons leads to action potential broadening, spike frequency adaptation, and spike failure from accumulated Na+ channel inactivation17. R420H and R417H may have a similar effect. In contrast, F448L is predicted to reduce the maximal firing rate of cerebellar neurons. Due to slower closing, after-hyperpolarization would be prolonged thus delaying the return to threshold and increasing the interspike interval. The differing effects of the mutations at the cellular level are consistent with the contrasting phenotypes in the two pedigrees. Whereas R420H reduces current amplitude with no change in channel properties, F448L alters key parameters of gating. The more severe functional alterations of the F448L are consistent with the earlier onset and more static disease course observed in the French pedigree.

The physiological properties of Kv3 channels provide tantalizing clues for potential mechanisms of neurodegeneration. Kv3 channels contribute significantly to the repolarization of dendritic Ca2+ spikes in Purkinje cells[17]. Longer duration spikes would increase Ca2+ influx, which may contribute to neuronal death. Additionally, the functional properties of Kv3.3 and Kv3.4 channels are modulated by reactive oxygen species[20-22]. Mutant Kv3.3 subunits may affect the ability of cerebellar neurons to cope with oxidative stress. Finally, morphological differentiation and the development of hallmark electrical properties are tightly linked in Purkinje cells. This raises the possibility that morphological and electrical maturation are interdependent phenomena[23]. Mutations that disrupt acquisition of appropriate electrical characteristics may cause subtle developmental defects that reduce the long-term viability of the neurons.

The results provided herein point to voltage-gated potassium channels as valid candidates for genes involved in phenotypes ranging from developmental disorders to late-onset neurodegenerative disease. It is likely that in vivo systems will be able to assess the consequences of mutant KCNC3 on three distinct but interrelated functions: cerebellar development, cerebellar function in the mature organism and the role of proper channel function preventing neuronal death. Both mutations show some intra-familial phenotypic variability highlighting the importance of compensatory mechanisms and the likely presence of other genetic and environmental modifiers. Further understanding of the role of voltage-gated K channels in cerebellar degeneration may lead to therapies aimed at modulating channel function not only to restore cerebellar function but also to reduce neurodegeneration.

Patients. A large Filipino family segregating a dominant trait for cerebellar ataxia was available for examination. There are eleven affected individuals spanning three generations. The living affecteds include the matriarch, eight individuals in generation two, and three individuals in generation three. In addition, there are five unaffected individuals in generation two, with one presumed unaffected and thirty-nine at-risk individuals in generation three, who have not yet been examined. After written informed consent was obtained, blood was collected and DNA extracted from fifteen family members. One affected individual from generation three was available for brain CT imaging.

Mutation and linkage analyses. Mutations in SCA1, 2, 3, 6, 7, 8, 12, 17, and DRPLA genes were eliminated as potential etiologies by direct PCR analysis (Pulst, S M. Neurogenetics: single gene disorders. J Neurol Neurosurg Psych 2003; 74:1608-1614). For SCA10, which has an expansion mutation that cannot be amplified by PCR, two normal alleles were observed in all affected individuals (Matsuura T, Yamagata T, Burgess D L, et al. Large expansion of the ATTCT pentanucleotide repeat in spinocerebellar ataxia type 10. Nat Genet 2000; 26(2):191-194). Linkage to loci for SCA5, 11, 13, 14, 16, 18, 19, 21, 23, and 25 were excluded by the observation of recombination events in close proximity to these loci.

In the genome-wide screen for linkage, a total of 377 fluorescent-tagged microsatellite markers in the human ABI Linkage Set v2.5 were utilized. These markers cover the entire genome with an average inter-marker genetic distance of 10 cM. Markers were run on an ABI 3100 using a capillary system.

To evaluate linkage in the 19q13 region, additional screening was done on the matriarch, eight affecteds and five unaffecteds in generation two, and three affected individuals in generation three as previously described (Zu L, Figueroa K P, Grewal R, Pulst, S M. Mapping of a new autosomal dominant spinocerebellar ataxia to chromosome 22. Am J Hum Genet 1999; 64(2):594-599). High resolution mapping was performed utilizing dinucleotide repeat markers obtained in the region of 19q13 from the Ensembl genome browser (http://www.ensembl.org, Jan. 15, 2005).

PCR was performed in a 20 µl reaction containing 100 ng of genomic DNA template, 100 pmol of each primer, 2.5 mM each dNTP, 2.5 mM MgC12, 0.25 U Taq polymerase, and buffer supplied by the vendor. The upstream primer was end-labeled with $\gamma$-$^{32}$P-ATP utilizing T4 Polynucleotide Kinase (Promega catalog #M4101) according to the manufacturer's instructions prior to PCR. The reaction conditions were as follows: initial denaturation at 95° C. for five minutes; 35 cycles of denaturing at 95° C. for 30 s, annealing at 62° C. for 30 s, and extension at 72° C. for 40 s; and a final extension at 72° C. for ten minutes. The entire reaction was performed in an M.J. Research PTC 200 thermocycler. The PCR products were analyzed by electrophoresis on a 6% denaturing polyacrylamide gel (National Diagnostics, Atlanta, Ga.) on an IBI BaseRunner 200 sequencer. Gels were exposed to Hyperfilm MP (Amersham Biosciences, England) and developed with a Kodak X-Omat automated processor.

Statistical analysis. Pair-wise and multi-point linkage analyses were performed with Genehunter (Kruglyak L, Lander E S. Faster multipoint linkage analysis using Fourier transformations, J Comput Biol 1998; 5:1-7; Kruglyak L, Daly M J, Reeve-Daly M P, Lander E S. Parametric and nonparametric linkage analysis: a unified multipoint approach. Am J Hum Genet 1996; 58:1347-1363) under the assumption of autosomal dominant inheritance and a disease allele frequency of 0.001 with penetrance set at 95 or 99%. The program size parameter (max bits) was fixed so that all genotyped subjects were included in the analyses. Genehunter also generated nonparametric results which were not substantively different from the parametric results presented here.

Results. Clinical features of the family. Nineteen individuals in the extended kindred were examined. Ten clinically affecteds from three generations were available for examination. The proband, an 82 year-old female is the oldest affected with disease onset at age 60 years. She has twelve living children: seven females of which four are affected, and five males of which three are affected. The seven affected offspring in generation two are between 46 and 65 years old, with age of onset ranging from 22 to 48 years (mean 36.4 years). The third generation has three affected individuals with mean onset at age 24.5 years. This includes a: 30 year-old female (onset age 26), 25 year-old male and a newly symptomatic male (onset ages 23 and 22 respectively). Cerebellar signs noted among the ten affecteds included gait ataxia, limb ataxia/dysmetria, titubation, hypotonia, dysarthria, and nystagmus. Two have mild, symmetric hyper-reflexia with no Babinski sign. Duration of disease ranges from 1-43 years with a mean of 13 years. The three oldest affecteds have the most severe ataxia (2 are wheelchair bound) with a disease duration of 24, 43, and 34 years, respectively. CT brain imaging (performed within the first year of symptoms) of the 30 year-old third generation female demonstrated mild cerebellar atrophy.

Exclusion of known loci. DNA repeat expansion mutations in SCA1, 2, 3, 6, 7, 8, 12, 17, and DRPLA were excluded by direct PCR analysis. Pentanucleotide repeat expansions in the SCA10 gene were excluded by demonstration of heterozygosity for two normal alleles in affecteds. Other SCA loci were excluded by linkage analysis. This included analysis with markers linked to SCA5, 11, 13, 14, 16, 18, 19, 21, 23, and 25. For each locus, at least one recombination event was observed within the linked region and for markers flanking the region.

Genome-wide screen. Due to the structure of the pedigree, approximately 15% of markers were non-informative as heterozygosity in individual I:2 was required for informativeness in generation II. Given this limitation, the results of the initial scan left several large gaps in the genome due to adjacent non-informative markers. Therefore, four genome areas (chromosomes 1, 14, 19, and 22) were further screened with CA repeat markers obtained from the Ensembl Genome Browser (http://www.ensembl.org, date of accession: Jan. 15, 2005).

After linkage to chromosomes 1, 14, and 22 was excluded, we re-examined linkage to the 19p13 region, as the genome scan failed to provide information in a large region defined by D19S902 at 53.02 Mb, and D19S210 at 61.71 Mb. This region was of interest as spinocerebellar ataxia type 13 had previously been mapped to 19q13.3-q13.4 in a large French family (Herman-Bert A, Stevanin G, Netter J C, et al. Mapping of spinocerebellar ataxia 13 to chromosome 19q13.3-q13.4 in a family with autosomal dominant cerebellar ataxia and mental retardation. Am J Hum Genet 2000; 67:229-235). Our genome scan identified several recombination events in affected individuals at D19S210 and one recombination in a generation II unaffected individual at marker D19S902.

Haplotypes for additional informative markers are shown in FIG. 1. Several markers including D19S904 showed no recombination events in affected or unaffected individuals. Obligate recombinants were detected for both D19S867 and D19S553. These markers define a physical candidate region of 1 Mb.

Figure 2:
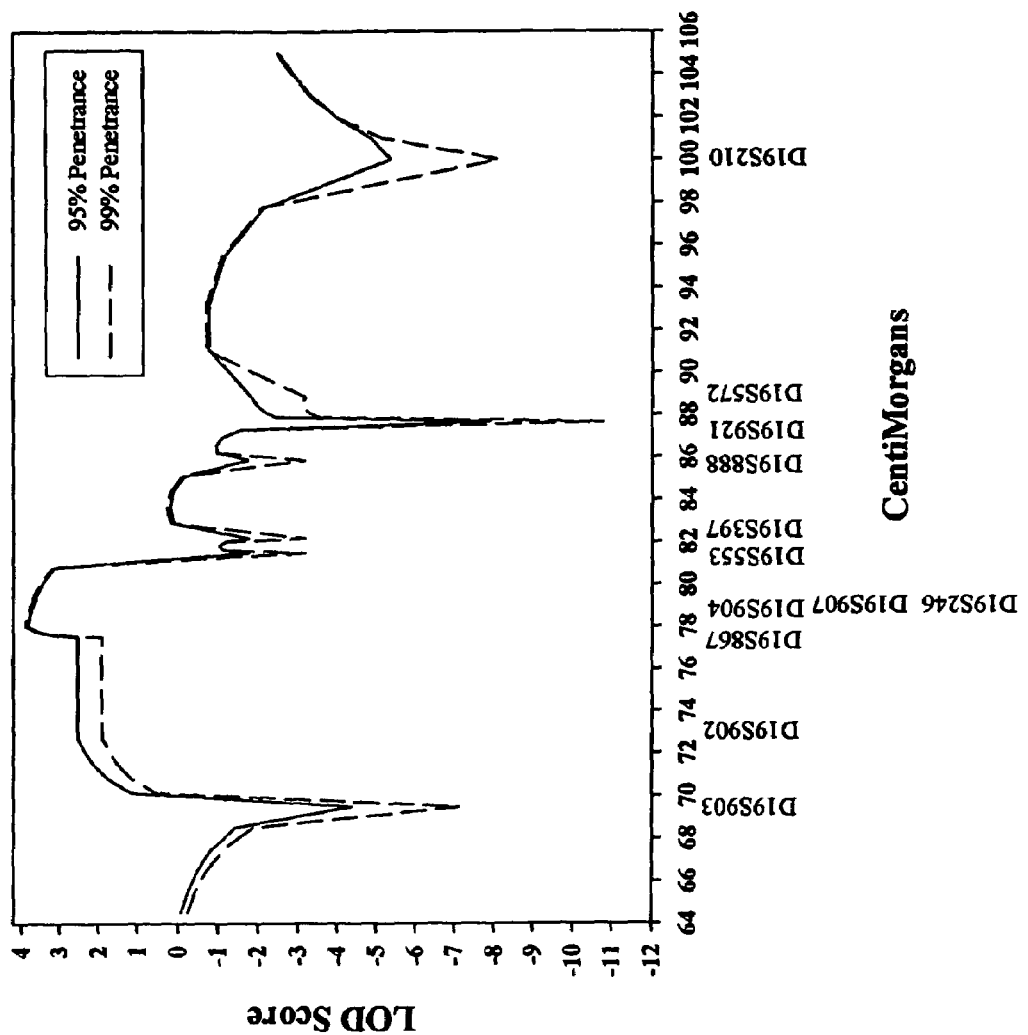
FIG. 2: Multipoint linkage analysis with twelve chromosome 19 markers. Max LOD is 3.83 at 78 cM. Linkage analysis performed assuming autosomal dominant inheritance with an allele frequency of 0.001 and 95% (solid line) or 99% (dashed line) penetrance. The genetic distances are based on the Marshfield genetic map.

The formal multi-point linkage analysis is shown in FIG. 2. The LOD-1 drop interval provides a most probable location of the disease gene in a 4 cM region near D19S904.

Discussion. The clinical phenotype of SCA13 is based on observations in one pedigree of French origin (Herman-Bert A, Stevanin G, Netter J C, et al. Mapping of spinocerebellar ataxia 13 to chromosome 19q13.3-q13.4 in a family with autosomal dominant cerebellar ataxia and mental retardation. Am J Hum Genet 2000; 67:229-235). Onset was in childhood and patients had mild mental retardation, and a relatively pure cerebellar ataxia with dysarthria, nystagmus, and discrete pyramidal features. The locus for this SCA spans an 8 cM region on 19q13.3-13.4 from 50.64-56.24 Mb (Généthon and Center for Medical Genetics, Marshfield Medical Research Foundation genetic maps) (Dib C, Faure S, Fizames C, et al. A comprehensive genetic map of the human genome based on 5,264 microsatellites. Nature 1996; 380(6570):152-4; Broman K W, Murray J C, Sheffield V C, White R L, Weber J L. Comprehensive human genetic maps: individual and sex-specific variation in recombination. Am J Hum Genet 1998; 63(3):861-9). The disease gene in the Filipino pedigree in this report maps to the distal segment of the SCA13 candidate region between genetic markers located at 55.46 and 56.24 Mb of the chromosome 19 genomic sequence.

Though the mechanism for disease in the majority of described SCAs is trinucleotide repeat expansion, evidence for clear anticipation is lacking in the description of the French SCA13 pedigree. Furthermore, neither rapid expansion detection (RED) analysis (Zander C, Thelaus J, Lindblad K, Karlsson M, Sjöberg K, Schalling M. Multivariate analysis of factors influencing repeat expansion detection. Genome Res 1998; 8:1085-1094) or Western blotting with an antibody which selectively recognizes polyglutamine sequences (Trottier Y, Lutz Y, Stevanin G et al. Polyglutamine expansion as a pathological epitope in Huntington's disease and four dominant cerebellar ataxias. Nature 1995; 378:403-406) found evidence for CAG expansion (commonly seen in diseases with anticipation) in SCA13.13 Our Filipino pedigree shows evidence of anticipation with mean age-of-onset falling from 36 years in generation II to 24 years in generation III. However, caution must be exercised in interpreting this finding as the number of observations in the individual pedigree is small. Moreover, anticipation has been described in Hereditary Spastic Paraplegia 4, in which the mutational event is not a pathological repeat expansion (Raskind W H, Pericak-Vance M A, Lennon F, Wolff J, Lipe H P, Bird T D. Familial spastic paraparesis: evaluation of locus heterogeneity, anticipation, and haplotype mapping of the SPG4 locus on the short arm of chromosome 2. Am J Med Genet 1997:74(1):26-36). Examination of the approximately million base-pair genomic sequence in the region defined by our family also failed to reveal areas of greater than ten uninterrupted CAG repeat tracts.

It was surprising that we had initially excluded the SCA13 locus on CHR19q based on the observation of several recombination events. In retrospect, it is evident that the chromosomal region shared by all affected individuals is unusually small. This made initial detection of linkage difficult, but resulted in an unusually small candidate region. Genes in the overlapping region defined by us and Herman-Bert et al. have been identified as potential candidates. These include genes belonging to families of transcription factors, trafficking proteins, and ion channels.

Assuming that the French SCA13 mutation and the mutation in the Filipino family are allelic, our results would greatly narrow the SCA13 candidate region. However, marked differences distinguish the previously described SCA13 phenotype and the phenotype in our pedigree. These include a much lower age of onset in SCA13 and mental retardation described in the French pedigree. In addition, there is the suggestion of anticipation in the Filipino family described here. Due to the rather invariant phenotypes described within the two families, the favored explanations are mutations in two distinct genes or allelic heterogeneity. Given the size of the SCA13 region it is possible that the causative genes are different in these two conditions. A similar phenomenon has been suggested in SCA15, where several overlapping loci lead to similar though clinically distinct phenotypes (Dudding T E, Friend K, Schofield P W, Lee S, Wilkinson I A, Richards R I. Autosomal dominant congenital non-progressive ataxia overlaps with the SCA15 locus. Neurology 2004; 63:2288-2292). Alternatively, the phenotypic differences may represent allelic heterogeneity or identical mutations with the observed differences due either to genetic background or environmental factors. Allelic heterogeneity has been well-described in SCA14 and includes disparate phenotypes such as early onset with mental retardation and pure late-onset cerebellar ataxia, reminiscent of the two phenotypes in the French and Filipino pedigrees mapping to 19q13 (Stevanin G, Hahn V, Lohmann E et al. Mutation in the catalytic domain of the protein kinase C γ and extension of the phenotype associated with spinocerebellar ataxia type 14. Arch Neurol 2004; 61:1242-1248; Chen D H, Cimino P J, Ranum L P W et al. The clinical and genetic spectrum of spinocerebellar ataxia 14. Neurology 2005; 64:1258-1260).

EXAMPLES

The following examples are provided to better illustrate the claimed invention and are not to be interpreted as limiting the scope of the invention. To the extent that specific materials are mentioned, it is merely for the purpose of illustration and is not intended to limit the invention. One skilled in the art may develop equivalent means or reactants without the exercise of inventive capacity and without departing from the scope of the invention.

Example 1

Patients. A Filipino family segregating a dominant trait for cerebellar ataxia was examined. There were eleven affected individuals including the proband, seven individuals in generation two, and three individuals in generation three. In addition, there were five unaffected individuals in generation two, with one unaffected and nineteen at-risk individuals in generation three. Blood was collected and DNA extracted from fifteen family members after informed consent was obtained.

Mutation and linkage analyses. To further evaluate linkage in the 19q13 region, additional markers were typed in the proband, seven affecteds and four unaffecteds in generation two, and three affecteds in generation three. High-resolution mapping was performed by PCR amplification of dinucleotide repeat markers obtained in the region of 19q13 from the Ensembl genome browser (release 31.35d). The PCR products were analyzed by electrophoresis on a 6% denaturing polyacrylamide gel.

Sequence analysis. DNA sequencing was performed using the ABI (Foster City, Calif.) "BigDye Terminator v3.1" cycle sequencing kit and the following protocol. To 5 ng (5 μl) purified PCR amplicon, 4 μl reaction pre-mix, 2 μl 5× sequencing buffer, 3.2 pmol (2 μl) appropriate primer, and 7 μl deinonized water were added to a 96-well microtitre plate and transferred to PCR thermocycler (MJ Research PTC-200) and cycled as follows: 1) 96° C. for 1 minute, 2) 96° C. for 10 seconds to 50° C. for 5 seconds to 60° C. for 4 minutes ×25 cycles. Sequencing products were then purified using ABI Centri-Sep™ spin columns. Resuspended samples were then electrophoresed on a 4.5% acrylamide gel in an ABI 377 DNA sequencer according to the manufacture's protocol. All sequences were analyzed using BioEdit's biological sequence alignment editor version 5.0.9.1.

Results

A three-generation Filipino family segregating a dominant ataxia with prominent cerebellar signs and symptoms as well as cerebellar atrophy on MR imaging (FIGS. 1a & b) was identified. The clinical and imaging phenotypes were typical of degenerative SCAs. A genome-wide linkage scan revealed a disease locus in a ~4 cM region of 19q13, with a 3.89 LOD score. This region partially overlapped the SCA13 locus (Herman-Bert, A. et al. Mapping of spinocerebellar ataxia 13 to chromosome 19q13.3-q13.4 in a family with autosomal dominant cerebellar ataxia and mental retardation. Am. J. Hum. Genet. 67, 229-235 (2000)), though the Filipino phenotype was clinically distinguishable from SCA13. For high-resolution mapping novel dinucleotide markers from the Ensembl genome browser (release 31.35d) were generated. The linkage region was reduced to ~900K bases. Haplotypes for the novel markers are shown in FIG. 4a. Several markers including D19S904 showed no recombination events. Obligate recombinants were detected for both D19S867 and D19S553, which defined a physical candidate region with the LOD-1 drop interval providing a probable location of the disease gene near D19S904. This region contained approximately forty candidate genes, including KCNC3. Direct sequencing revealed two missense mutations in exon 2. The Filipino pedigree contained 1554G→A, encoding R420H in the third conserved arginine residue in S4 (FIG. 4c). The French pedigree contained 1639C→A, encoding F448L near the cytoplasmic end of S5 (FIG. 4d).

Example 2

Among voltage-gated $K^+$ channels, the functional properties of Kv3 channels are distinct. Kv3 channels activate in a more depolarized range and close much more rapidly compared to other Kv channels (Rudy, B. & McBain, C. J. Kv3 channels: voltage-gated K+ channels designed for high-frequency repetitive firing. Trends Neurosci. 9, 517-526 (2001)). These properties facilitate high frequency firing of action potentials with little or no adaptation, a characteristic of neuronal populations found in the mammalian neocortex, hippocampus, auditory nuclei, and cerebellum. Like other voltage-gated $K^+$ channels, Kv3 channels are tetramers. Different Shaw family subunits are able to co-assemble with each other, but not with subunits from other Kv subfamilies (Covarrubias, M., Wei, A., & Salkoff, L. Shaker, Shal, Shab, and Shaw express independent K+ current systems. Neuron 7, 763-773 (1991); Shen, N. V. & Pfaffinger, P. J. Molecular recognition and assembly sequences involved in the subfamily-specific assembly of voltage-gated K+ channel subunit proteins. Neuron 14, 625-633 (1995)).

Each subunit has six transmembrane segments and a re-entrant loop (FIG. 5a). The first four transmembrane segments, S1-S4, constitute the voltage sensor domain, whereas the last two segments, S5 and S6, and the re-entrant loop form the ion-selective pore (Long, S. B., Campbell, E. B., & MacKinnon, R. Crystal structure of a mammalian voltage-dependent Shaker family K+ channel. Science 309, 897-890 (2005)). The Filipino mutation is located in S4, the main voltage-sensing element and changes one of the multiple positively charged residues that respond to changes in membrane potential (Aggarwal, S. K. & MacKinnon, R. Contribution of the S4 segment to gating charge in the Shaker K+ channel. Neuron 16, 1169-1177 (1996); Seoh, S. A., Sigg, D., Papazian, D. M., & Bezanilla, F. Voltage-sensing residues in the S2 and S4 segments of the Shaker K+ channel. Neuron 16, 1159-1167 (1996)).

The French mutation is in the cytoplasmic end of S5, which is involved in coupling voltage-sensor conformational changes with opening and closing of the pore (Shieh, C. C., Klemic, K. G., & Kirsch, G. E. Role of transmembrane segment S5 on gating of voltage-dependent K+ channels. J. Gen. Physiol. 109, 767-778 (1997)). The depolarized voltage dependence and rapid deactivation that are characteristic of Kv3 channels are related properties conferred by specific amino acid residues in the voltage sensor and S5 (Smith-Maxwell, C. J., Ledwell, J. L., & Aldrich, R. W. Uncharged S4 residues and cooperativity in voltage-dependent potassium channel activation. J. Gen. Physiol. 111, 421-439 (1998)). Importantly, KCNC3 protein sequences in S4 and S5 are 100% conserved amongst phyla, suggesting strong selection for the specialized role of these channels (FIG. 5b). Consistent with this observation, screening over four hundred alleles from normal individuals of Filipino or Anglo-European descent revealed no polymorphisms at either site, but revealed an additional mutation, R417H, also mapping to the S4 segment of KCNC3, involved in neurodegenerative ataxia.

Figure 6:
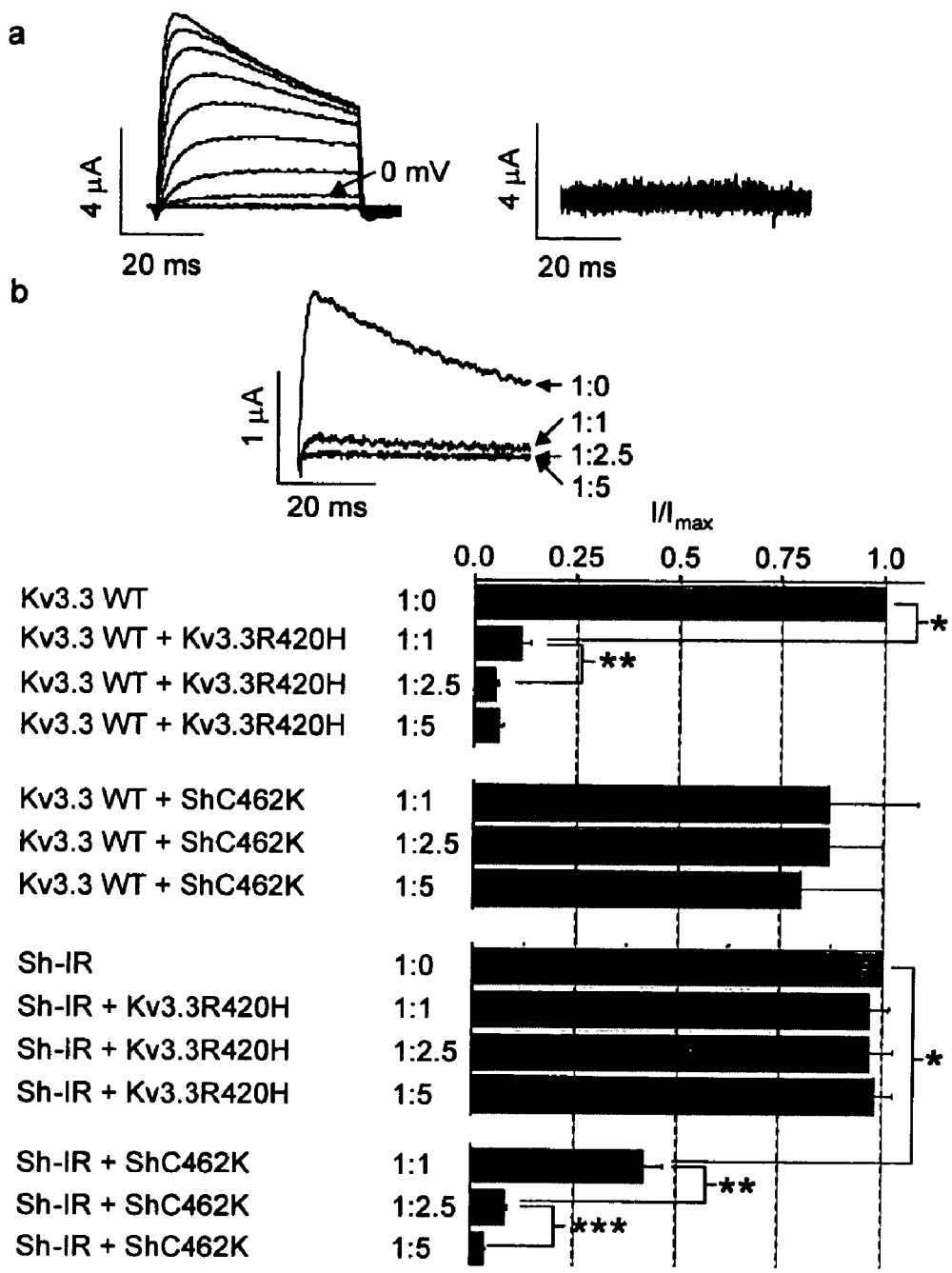
FIG. 6: Subfamily-specific dominant negative effect of R420H. a, Current traces from wildtype (left) and R420H (right) channels were evoked by stepping from −90 mV to voltages ranging from −80 to +70 mV in 10 mV increments. In wildtype, partial inactivation was observed at potentials greater than +20 mV. The 0 mV record from wildtype channels is labeled for comparison to FIG. 4a. b, Upper panel shows representative current traces evoked by stepping from −90 mV to +60 mV for wildtype Kv3.3 expressed alone (1:0) or in the presence of R420H at the indicated ratios. Lower panel plots normalized peak current amplitudes at +60 mV for Kv3.3 wildtype expressed alone (1:0), or expressed with Kv3.3-R420H or Shaker-C462K (Sh-C462K, a non-functional Shaker subunit24) at the indicated ratios. Also shown are peak current amplitudes at +60 mV for inactivation-removed Shaker (Sh-IR) expressed alone (1:0), or expressed with Kv3.3-R420H or Sh-C462K at the indicated ratios. Values are provided as mean ±SEM, n=4-10. Statistical significance tested by one way ANOVA, p<0.05: *, different from 1:0; , different from 1:1; *, different from 1:2.5.

To investigate the functional consequences of the SCA 13 mutations, wildtype and mutant KCNC3 alleles were expressed in *Xenopus laevis* oocytes and channel activity was recorded using a two electrode voltage clamp. Activation of the wild type Kv3.3 channel was detected at −10 mV and more positive potentials (FIG. 6a). Upon repolarization to −90 mV, the channel closed quickly. In contrast, expression of R420H resulted in no detectable channel activity (FIG. 6a). Co-expression of wildtype Kv3.3 and R420H subunits led to suppression of current amplitude consistent with a dominant negative effect (FIGS. 6b & c). R420H did not suppress the expression of Shaker, a member of the Kv1 family (FIG. 6c). These results indicated that Kv3 subfamily-specific co-assembly of wildtype and mutant subunits produced non-functional channels.

Example 3

Electrophysiology. The coding region of a human Kv3.3 cDNA clone (Rae, J. L., & Shepard, A. R. Kv3.3 potassium channels in lens epithelium and corneal endothelium. Exp. Eye. Res. 70, 339-348 (2000) was transferred into the Bluescript II SK vector. RNA was transcribed and injected into *Xenopus* oocytes for two electrode voltage clamp analysis using standard methods (Silverman, W. R., Tang, C. Y., Mock, A. F., Huh, K. B., & Papazian, D. M. Mg (2+) modulates voltage-dependent activation in ether-a-go-go potassium channels by binding between transmembrane segments S2 and S3. J. Gen. Physiol. 116, 663-677 (2000)). Currents were recorded 48 to 72 h post injection in a bath solution containing 4 mM KCl, 85 mM NaCl, 1.8 mM $CaCl_2$, 10 mM HEPES, pH 7.2. To record tail currents, the bath solution was switched to 89 mM RbCl, 2.4 mM $NaHCO_3$, 0.82 mM $Ca(NO_3)_2$, 0.41 mM $CaCl_2$, 10 mM HEPES, pH 7.2. For dominant negative experiments, 1 ng of Kv3.3 or Shaker IR RNA was injected, in the absence or presence of the indicated ratio of mutant RNA.

Figure 7:
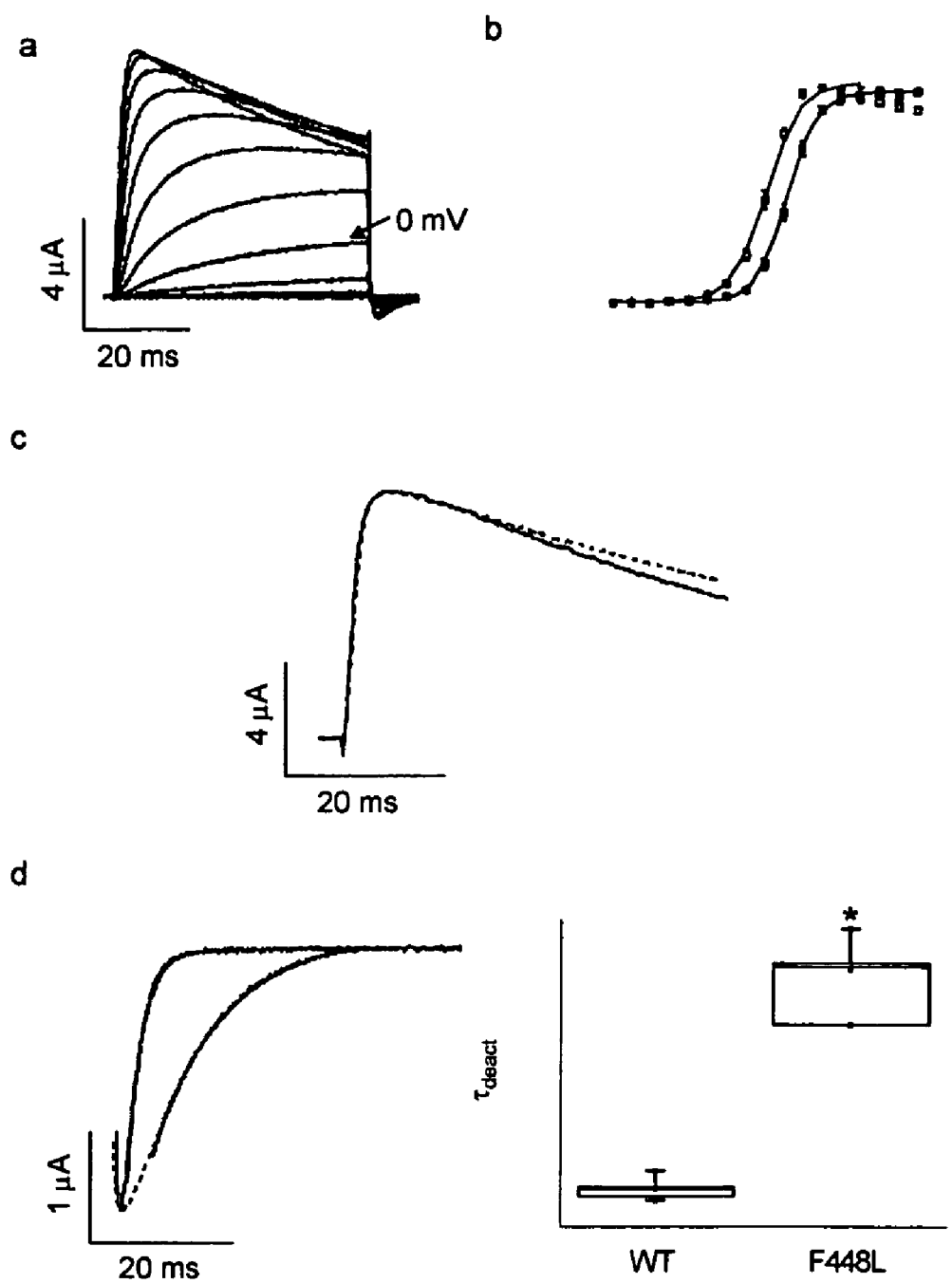
FIG. 7: Altered gating in F448L. a, Current traces from F448L channels were evoked by stepping from −90 mV to voltages ranging from −80 to +70 mV in 10 mV increments. The 0 mV record is labeled for comparison to FIG. 3a. b, To determine the probability of opening (Po) as a function of voltage, wildtype or F448L currents were evoked by stepping from −90 mV to various test potentials, followed by repolarization to −90 mV. The bath solution contained 89 mM Rb+. Isochronal tail current amplitudes were normalized to the maximal value obtained in the experiment and plotted versus test potential. Wildtype, filled squares; F448L, open squares. Values are provided as mean±SEM, n=6 (F448L) or 7 (wildtype). The data sets were fitted with single Boltzmann functions (solid lines), which yielded midpoint voltages of 2.8±1.0 mV and −9.6±1.3 mV and slope factors of 7.6±0.3 and 7.6±0.1 for wildtype and F448L channels, respectively. Midpoint voltages were significantly different, p<0.05 by one way ANOVA. c, Representative current traces obtained at +60 mV have been scaled and overlaid for wildtype (solid) and F448L (dashed). d, Left panel: Representative tail currents from wildtype (solid) and F448L (dashed), recorded in an 89 mM Rb+bath solution, were obtained by stepping from +20 to −90 mV. The traces have been scaled and overlaid. Tail currents were fitted with a single exponential function (solid lines) to obtain values for the deactivation time constant, τdeact. Right panel: Box plot of τdeact for wildtype and F448L. Mean values±SEM were 2±0.2 ms and 13.3±1.0 for wildtype (n=7) and F448L (n=4), respectively. Values of τdeact differed significantly by one way ANOVA: *, p<0.05.

Results: Expression of F448L produced channels with altered gating. Activation of F448L was detected at −20 mV, compared to −10 mV for wildtype (FIG. 7a). Analysis of the probability of opening as a function of voltage confirmed that activation was shifted ~13 mV toward the hyperpolarized direction (FIG. 7b). Activation kinetics of F448L and wildtype were similar at voltages where both have a maximal open probability (FIG. 7c). However, deactivation kinetics of F448L were dramatically slower. Tail currents were recorded after repolarization to −90 mV using an 89 mM $Rb^+$ bath solution, and fitted with a single exponential component (FIG. 7d). This revealed a ~7-fold slowing of channel closure in the F448L channel. The hyperpolarized shift in the probability of opening and the slower rate of deactivation are related findings indicating that F448L increases the relative stability of the open state. F448L makes the properties of Kv3.3 channels more similar to those of Shaker and other channels that normally have a leucine residue in the analogous position (FIG. 5b).

Although abnormalities of ion channels are rare causes of diseases of the heart, kidney, and skeletal muscle (Graves, T. D., & Hanna M. G. Neurological channelopathies. Postgrad. Med. J. 81, 20-32 (2005); Dworakowska B., & Dolowy K. Ion channels-related diseases. Acta Bioch. Pol. 47, 685-703 (2000), KCNC3 was not a likely candidate for a degenerative ataxia, as potassium channel mutations are not associated with neurodegeneration, but with episodic phenomena such as epilepsy and episodic ataxia. Furthermore, KCNC3 deficiency in the mouse did not produce a phenotype (Espinosa, F., et al. Alcohol hypersensitivity, increased locomotion, and spontaneous myoclonus in mice lacking the potassium channels Kv3.1 and Kv3.3. J. Neurosci. 21, 6657-6665 (2001).

Unlike other SCA genes implicated in neurodegeneration, the physiological functions of Kv3 channels in the cerebellum have been extensively studied and are reasonably well understood (Martina, M., Yao, G. L., & Bean, B. P. Properties and functional role of voltage-dependent potassium channels in dendrites of rat cerebellar Purkinje neurons. J. Neurosci. 23, 5698-5707 (2003); McKay, B. E., & Turner, R. W. Kv3 K+ channels enable burst output in rat cerebellar Purkinje cells. Eur. J. Neurosci. 20, 729-739 (2004). Kv3.3 is expressed in cerebellar granule cells, Purkinje cells, and deep cerebellar neurons, where it may form heteromultimeric channels by co-assembly with Kv3.1 and/or Kv3.4 (Goldman-Wohl, D. S., Chan, E., Baird, D., & Heintz, N. Kv3.3b: a novel Shaw type potassium channel expressed in terminally differentiated cerebellar Purkinje cells and deep cerebellar nuclei. J. Neurosci. 14, 511-522 (1994); Weiser, M. et al. Differential expression of Shaw-related K+ channels in the rat central nervous system. J. Neurosci. 14, 949-972 (1994)). In Purkinje cells, Kv3 channels are involved in repolarizing both somatic $Na^+$ spikes and dendritic $Ca^{3+}$ spikes. Kv3 channels are essential for fast spiking in neurons that fire hundreds of action potentials per second with little or no frequency adaptation. Because of their depolarized activation range, Kv3 channels open only during action potentials, contribute to fast repolarization, and thus promote recovery of Na+ channels from inactivation. Fast deactivation of Kv3 channels limits the time course of the after-hyperpolarization, thereby shortening the refractory period.

In all likelihood, the SCA13 mutations disrupt the firing properties of fast spiking cerebellar neurons. Although the Kv3.3 knock-out mouse has no obvious motor phenotype, the double Kv3.1/Kv3.3 knock-out has dramatic symptoms, including tremor and severe ataxia. Because R420H is expected to suppress the functional expression of Kv3.3 as well as other subunits in the Kv3 family, this mutation may be more comparable to the double knockout. Pharmacological suppression of Kv3 activity in cerebellar neurons leads to action potential broadening, spike frequency adaptation, and spike failure from accumulated Na+ channel inactivation. R420H and R417H may have a similar effect. In contrast, F448L is predicted to reduce the maximal firing rate of cerebellar neurons. Due to slower closing, after-hyperpolarization would be prolonged thus delaying the return to threshold and increasing the interspike interval. The differing effects of the mutations at the cellular level are consistent with the contrasting phenotypes in the two pedigrees. Whereas R420H reduces current amplitude with no change in channel properties, F448L alters key parameters of gating. The more severe functional alterations of the F448L are consistent with the earlier onset and more static disease course observed in the French pedigree.

The physiological properties of Kv3 channels provide tantalizing clues for potential mechanisms of neurodegeneration. Kv3 channels contribute significantly to the repolarization of dendritic $Ca^{2+}$ spikes in Purkinje cells. Longer duration spikes would increase $Ca^{2+}$ influx, which may contribute to neuronal death. Additionally, the functional properties of Kv3.3 and Kv3.4 channels are modulated by reactive oxygen species (Ruppersberg, J. P. et al. Regulation of fast inactivation of cloned mammalian IK(A) channels by cysteine oxidation. Nature 352, 711-714 (1991); Vega-Saenz de Miera E and Rudy B (1992) Biochem Biophys Res Comm 186, 1681-1687; Duprat, F. Susceptibility of cloned K+ channels to reactive oxygen species. Proc. Natl. Acad. Sci. U.S.A. 92, 11796-11800 (1995)). Mutant Kv3.3 subunits may affect the ability of cerebellar neurons to cope with oxidative stress. Finally, morphological differentiation and the development of hallmark electrical properties are tightly linked in Purkinje cells. This raises the possibility that morphological and electrical maturation are interdependent phenomena (McKay, B. E., & Turner, R. W. Physiological and morphological development of the rat cerebellar Purkinje cell. J. Physiol. epub ahead of print (2005)). Mutations that disrupt acquisition of appropriate electrical characteristics may cause subtle developmental defects that reduce the long-term viability of the neurons.

Our results point to voltage-gated potassium channels as valid candidates for genes involved in phenotypes ranging from developmental disorders to late-onset neurodegenerative disease. It is likely that in vivo systems will be required to assess the consequences of mutant KCNC3 on three distinct but interrelated functions: cerebellar development, cerebellar function in the mature organism and the role of proper channel function preventing neuronal death. Both mutations show some intra-familial phenotypic variability highlighting the importance of compensatory mechanisms and the likely presence of other genetic and environmental modifiers. Further understanding of the role of voltage-gated K channels in cerebellar degeneration may lead to therapies aimed at modulating channel function not only to restore cerebellar function but also to reduce neurodegeneration.

Example 4

Potassium channels are ubiquitous in nature and play significant roles in nerve and muscle tissue electrical excitability in mammals. Potassium channelopathies are known to cause episodic neurological diseases in humans. The present invention has identified mutations in the voltage-gated potassium channel, KCNC3 (Kv3.3), which cause the neurodevelopmental/degenerative disorder SCA13. One mutation, located in the voltage-sensing domain, causes a dominant negative effect. A second mutation, located in the domain effecting voltage-sensor conformational changes conferring pore opening and closing, shifts the activation curve more negative and slows channel closing. This characterization expands the role of potassium channels in neurological diseases and suggests their importance in both neurodevelopment and neurodegeneration.

Potassium channels influence many aspects of electrical excitability in nerve and muscle, and mutations in their genes have been described in episodic neurological diseases[1-3]. The present invention now demonstrates that K+ channel mutations also cause a neurodevelopmental/degenerative disease, spinocerebellar ataxia. In a Filipino pedigree with adult-onset ataxia, the causative gene maps to 19g13, overlapping the SCA 13 locus previously described in a French pedigree with childhood-onset mental retardation, ataxia and seizures[4]. This region contains KCNC3 (K0.3), which encodes a voltage-gated Shaw potassium channel with enriched cerebellar expressions. Sequencing KCNC3 revealed mutations 1554G→A (R420H) in the Filipino and 1639C→A (F448L) in the French pedigrees. Both mutations alter KCNC3 function in the *Xenopus* oocyte expression system. KCNC3 R420H, located in the voltage sensor of the channel[6], has no detectable channel activity when expressed alone and a strong dominant negative effect when co-expressed with wildtype KCNC3. KCNC3 F448L shifts the activation curve in the negative direction and slows channel closing by ~7-fold. Thus, R420H and F448L mutations are expected to change the output characteristics of fast-spiking cerebellar neurons, where KCNC channels confer capacity for high frequency firing. The present invention has identified voltage-gated potassium channels as valid candidates for genes involved in phenotypes ranging from developmental disorders to adult-onset neurodegeneration.

Dominant spinocerebellar ataxias (SCA) are heterogeneous neurological diseases with phenotypes consisting of cerebellar ataxia, extrapyramidal signs, dysarthria, oculomotor abnormalities, motor neuron signs, cognitive decline, epilepsy, autonomic dysfunction, sensory deficits, and psychiatric manifestations[7,8]. Twenty-six SCA loci are described, and for ten the causative gene or mutation has been determined. Little is known about the normal function of most SCA genes, though the majority represent polyglutamine (polyQ) expansion diseases.

Figure 4:
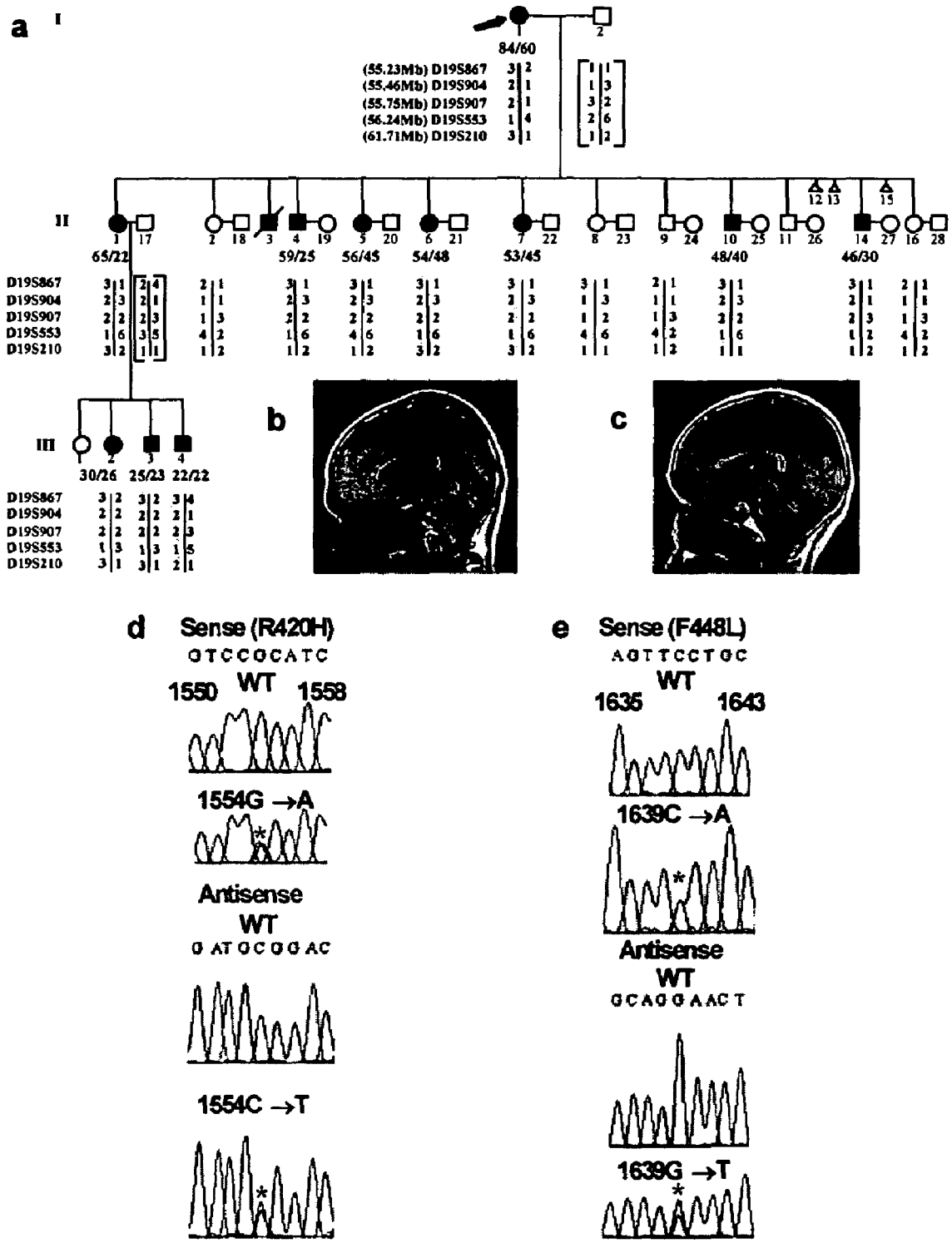
FIG. 4: Filipino pedigree with autosomal dominant spinocerebellar ataxia. a, Filipino pedigree and haplotypes for five informative chromosome 19 markers assuming the smallest number of recombination events. Note critical recombination events in individuals II-5 and II-8. Haplotype blocks segregating with disease are shaded. Affected individuals are represented by darkened symbols. Age at examination and age-of-onset are shown in bold above the haplotype. Proband denoted by arrow. Sagittal T1 sequence MR images of individuals III-2 (b) and II-1 (c) reveal marked cerebellar volume loss. Duration of disease is 16 years in III-2 and 43 years in II-1, likely accounting for the more pronounced degeneration in II-1. d, and e, DNA sequence analysis revealed the 1554G→A, and 1639C→A point mutations in exon 2 of Kv3.3 causing SCA13. Both sense and anti-sense strands are shown, as well as wild-type (WT) sequence. Mutations designated with asterisk.

A three-generation Filipino family segregating an adult-onset dominant ataxia with prominent cerebellar signs and symptoms[9] as well as cerebellar atrophy on magnetic resonance imaging (FIG. 4) has previously been identified. The clinical and imaging phenotypes were typical of degenerative SCAs. A genome-wide linkage scan revealed a disease locus in a ~4 cM region of 19g13, with a 3.89 LOD score. This region partially overlapped the SCA13locus[4] mapped in a French pedigree with mild mental retardation, early-onset ataxia, and slow progression, though the Filipino phenotype was clinically distinguishable from SCA 13. Through high-resolution mapping, the linkage region was reduced to ~900K bases. Haplotypes are shown in FIG. 4.

Several markers showed no recombination events. Obligate recombinants were detected for both DI 9S867 and DI 9S553, which defined a physical candidate region with the LOD-1 drop interval providing a probable location of the disease gene near D19S904. This region contained approximately forty candidate genes, including KCNC3.

Figure 5:
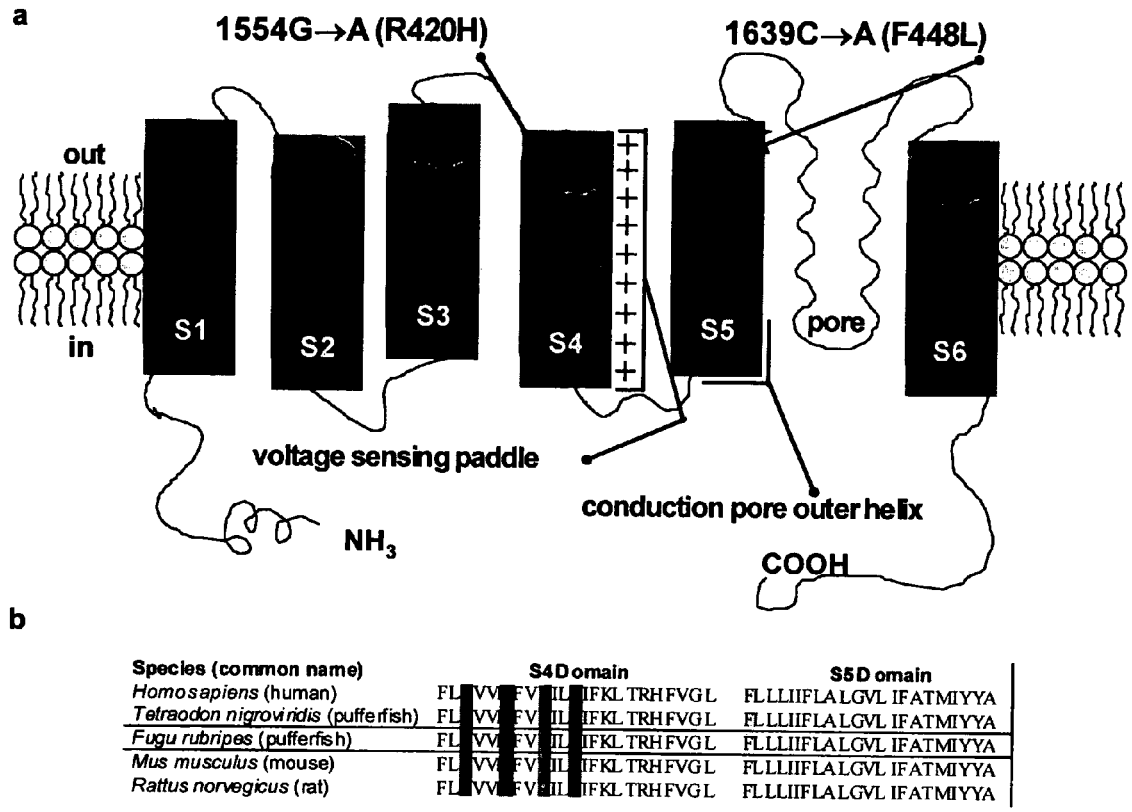
FIG. 5: Functional motifs and sequence comparisons of Shaw-subfamily voltage-gated potassium channels. a, Schematic of a single Kv3.3 subunit illustrating the six functional domains and re-entrant loop. Segments S1-S4 form the voltage sensor domain. Positively charged arginine residues in S4 sense changes in voltage. Segments S5, S6, and the re-entrant loop form the ion-selective pore. S5 forms the pore outer helix and functions to couple voltage-sensor conformational changes with pore opening and closing. SCA13 mutations are shown with arrows. b, Amino acid sequence comparison across species of the Kv3.3 S4 and S5 functional domains reveals 100% conservation. Yellow highlights the R420H(S4) and F448L (S5) mutations. Red highlights the positively charged arginine residues occurring every third position.

Among voltage-gated K+ channels, the functional properties of Kv3 channels are distinct. Kv3 channels activate in a more depolarized range and close much more rapidly than other Kv channels 10. These properties facilitate high frequency firing of action potentials with little or no adaptation, a characteristic of neuronal populations found in the mammalian neocortex, hippocampus, auditory nuclei, and cerebellum[10]. Like other voltage-gated K+ channels, Kv3 channels are tetramers. Different Shaw family subunits are able to co-assemble with each other, though not with subunits from other Kv subfamilies[11,12]. Each subunit has six transmembrane segments and a re-entrant loop (FIG. 5A). The first four transmembrane segments, S1-S4, constitute the voltage sensor domain, whereas the last two segments, S5 and S6, and the re-entrant loop form the ion-selective pore[13]. The depolarized voltage dependence and rapid deactivation that are characteristic of Kv3 channels are related properties conferred by specific amino acid residues in the voltage sensor and S5[14,15]. The Filipino mutation (FIG. 4 E) is located in S4 (FIG. 5A), the main voltage-sensing element, and changes one of the positively charged residues that respond to changes in membrane potential[6,16]. The French mutation (FIG. 4F) is at the cytoplasmic end of S5 (FIG. 5A), which is involved in coupling voltage-sensor conformational changes with opening and closing of the pore[14]. These mutations, leading to highly penetrant phenotypes, were identified in all affected individuals though not in clinically normal family members. Consistent with this observation, screening over four hundred alleles from normal individuals of Filipino or Anglo-European descent revealed no polymorphisms at either site. Importantly, KCNC amino acid sequences in S4 and S5 are 100% conserved amongst phyla, suggesting strong selection for the highly specialized role of these channels (FIG. 5).

To investigate the functional consequences of the SCA13 mutations, wildtype and mutant KCNC3 alleles were expressed in *Xenopus laevis* oocytes and channel activity was recorded using a two electrode voltage clamp. Activation of the wildtype Kv3.3 channel was detected at –10 mV and more positive potentials (FIG. 6A). Upon repolarization to –90 mV, the channel closed quickly. In contrast, expression of R420H resulted in no detectable channel activity (FIG. 6A). Co-expression of wildtype Kv3.3 and R420H subunits led to suppression of current amplitude consistent with a dominant negative effect (FIG. 6B). R420H did not suppress the functional expression of Shaker, a member of the Kv1 family (FIG. 6B). These results indicated that Kv3 subfamily-specific co-assembly of wildtype and mutant subunits produced non-functional channels.

Expression of F448L produced channels with altered gating. Activation of F448L was detected at –20 mV, compared to –10 mV for wildtype (FIG. 7A). Analysis of the probability of opening as a function of voltage confirmed that activation was shifted ~13 mV toward the hyperpolarized direction (FIG. 7B). Activation kinetics of F448L and wildtype were similar at voltages where both have a maximal open probability (FIG. 7C). However, deactivation kinetics of F448L were dramatically slower. Tail currents were recorded after repolarization to –90 mV using an 89 mM Rb+bath solution, and fitted with a single exponential component (FIG. 7D). This revealed a ~7-fold slowing of channel closure in F448L. The hyperpolarized shift in the probability of opening and the slower rate of deactivation are related findings indicating that F448L increases the relative stability of the open state. F448L makes the properties of Kv3.3 channels more similar to those of Shaker and other channels that normally have a leucine residue in the analogous position (FIG. 5B).

Unlike other genes implicated in spinocerebellar ataxias, the physiological functions of Kv3 channels in the cerebellum have been extensively studied and are reasonably well understood[17,18]. Kv3.3 is expressed in cerebellar granule cells, Purkinje cells, and deep cerebellar neurons, where it may form heteromultimeric channels by co-assembly with Kv3.1 and/or Kv3.4[19,20]. In Purkinje cells, Kv3 channels are involved in repolarizing both somatic Na+ spikes and dendritic Ca2+ spikes[18]. Kv3 channels, including KCNC1 (Kv3.1), KCNC2 (Kv3.2), KCNC3 (Kv3.3), and KCNC4 (Kv3.4) are essential for fast spiking in neurons that fire hundreds of action potentials per second with little or no frequency adaptation[10]. Because of their depolarized activation range, Kv3 channels open only during action potentials, contribute to fast repolarization, and thus promote recovery of Na$^+$ channels from inactivation. Fast deactivation of Kv3 channels limits the time course of the after-hyperpolarization, thereby shortening the refractory period.

In all likelihood, the SCA13 mutations disrupt the firing properties of fast spiking cerebellar neurons. Although the Kv3.3 knock-out mouse has no obvious motor phenotype, the double Kv3.1/Kv3.3 knock-out has dramatic symptoms, including tremor and severe ataxia[21]. Because R420H is expected to suppress the functional expression of Kv3.3 as well as other subunits in the Kv3 family, this mutation may be more comparable to the double knockout. Pharmacological suppression of Kv3 activity in cerebellar neurons leads to action potential broadening, spike frequency adaptation, and spike failure from accumulated Na+ channel inactivation[18]. R420H may have a similar effect. In contrast, F448L is predicted to reduce the maximal firing rate of cerebellar neurons. Due to slower closing, after-hyperpolarization would be prolonged thus delaying the return to threshold and increasing the interspike interval. The differing effects of the mutations at the cellular level may portend the contrasting phenotypes between the two pedigrees.

The physiological properties of Kv3 channels provide tantalizing clues for potential mechanisms of neurodegeneration. Kv3 channels contribute significantly to the repolarization of dendritic Ca2+ spikes in Purkinje cells[18]. Longer duration spikes would increase Ca+ influx, which may contribute to neuronal death. Additionally, the functional properties of Kv3.3 and Kv3.4 channels are modulated by reactive oxygen species[22-24].

Mutant Kv3.3 subunits may affect the ability of cerebellar neurons to cope with oxidative stress. Finally, morphological differentiation and the development of hallmark electrical properties are tightly linked in Purkinje cells. This raises the possibility that morphological and electrical maturation are interdependent phenomena[25]. Mutations that disrupt acquisition of appropriate electrical characteristics may cause subtle developmental defects that reduce the long-term viability of the neurons.

The present invention identifies KCNC3 mutations as causative for SCA13 and demonstrates to the importance of voltage-gated potassium channels in phenotypes ranging from developmental disorders to late-onset neurodegenerative disease. It is likely that in vivo systems will be able to assess the consequences of mutant KCNC3 on three distinct but interrelated functions: cerebellar development, cerebellar function in the mature organism and the role of proper channel function preventing neuronal death. Both mutations show some intra-familial phenotypic variability highlighting the importance of compensatory mechanisms and the likely presence of other genetic and environmental modifiers. Further understanding of the role of voltage-gated K channels in cerebellar degeneration may lead to therapies aimed at modulating channel function to both restore cerebellar function and reduce neurodegeneration.

Methods

Patients. A Filipino family segregating a dominant trait for cerebellar ataxia was examined. There are eleven affected individuals including the proband, seven individuals in generation two, and three individuals in generation three. In addition, there are five unaffected individuals in generation two, with one unaffected and nineteen at-risk individuals in generation three. Blood was collected and DNA extracted from fifteen family members after informed consent was obtained.

Mutation and linkage analyses. To further evaluate linkage in the 19q13 region, additional markers were typed in the proband, seven affecteds and four unaffecteds in generation two, and three affecteds in generation three. High-resolution mapping was performed by PCR amplification of dinucleotide repeat markers obtained in the region of 19g13 from the Ensembl genome browser (release 31.35d). The PCR products were analyzed by electrophoresis on a 6% denaturing polyacrylamide gel.

Sequence analysis. DNA sequencing was performed using the ABI (Foster City, Calif.) "BigDye Terminator v3.1" cycle sequencing kit and the following protocol. To 5 ng (5 ml) purified PCR amplicon, 4 ml reaction pre-mix, 2 ml 5× sequencing buffer, 3.2 pmol (2 ml) appropriate primer, and 7 ml deinonized water were added to a 96-well microtitre plate and transferred to PCR thermocycler (MJ Research PTC-200) and cycled as follows: 1) 96° C. for 1 minute, 2) 96° C. for 10 seconds to 50° C. for 5 seconds to 60° C. for 4 minutes ×25 cycles, 3).

Sequencing primers as follows:
SEQ ID NO: 1: Exon 1-5'TAG GTG AGG GCG TGC GAT CTG TT
SEQ ID NO: 2: 3'GCC CGC GGA AGG ACG AGA C
SEQ ID NO: 3: 5'CTC CCA CCC AAT CCC GTC GGT C
SEQ ID NO: 4: 3'GCG ATG CTG CCG GTA GGT CAT CC
SEQ ID NO: 5: 5'TC GCG TAC GTG CTC AAC TAC TA
SEQ ID NO: 6: 3'TGG GGA AGA GGC TTC TAG GAG
SEQ ID NO: 7: Exon 2- 5'GGG CAC TGG AAG GGT CTT
SEQ ID NO: 8: 3'ATG GGG ATG TTC TTG AAG TAG GT
SEQ ID NO: 9: 5'CGC CAC CAT GAT TTA CTA CGC
SEQ ID NO: 10: 3'TTT TTC TCC CTC ACC TCT TCG AC
SEQ ID NO: 11: Exons 3/4- 5'ATC TTG CCC CAC CGC GTG TTC A
SEQ ID NO: 12: 3'CGG TCA GTG GGG GCT GCA TGT TC
SEQ ID NO: 13: Exon 5- 5'GAA ATG ATC CCG GCG GCG TTT CT
SEQ ID NO: 14: 3'GGC AGC AAG GCG GGA TGG TG Sequencing products were then purified using ABI Centri-Sep'm spin columns. Resuspended samples are then electrophoresed on a 4.5% acrylamide gel in an ABI 377 DNA sequencer according to the manufacture's protocol. All sequences were analyzed using BioEdit's biological sequence alignment editor version 5.0.9.1.

Electrophysiology. The coding region of human Kv3.3 cDNA clone was transferred into the Bluescript II SK vector. RNA was transcribed and injected into *Xenopus* oocytes for two electrode voltage clamp analysis using standard methods28. Currents were recorded 48 to 72 h post injection in a bath solution containing 4 mM KCl, 85 mM NaCl, 1.8 mM $CaCl_2$, 10 mM HEPES, pH 7.2. To record tail currents, the bath solution was switched to 89 mM RbCl, 2.4 mM NaHCO3, 0.82 mM Ca(NO3)2, 0.41 mM $CaCl_2$, 10 mM HEPES, pH 7.2. For dominant negative experiments, 1 ng of Kv3.3 or Shaker IR RNA was injected, in the absence or presence of the indicated ratio of mutant RNA.

REFERENCES

1. T. D. Graves and M. G. Hanna, Postgrad. Med. J. 81, 20 (2005).
2. B. Dworakowska and K. Dolowy, Acta Bioch. Pol. 47, 685 (2000).
3. J. C. Mulley, I. E. Scheffer, S. Petrou, S. F. Berkovic, Curr. Opin. Neurol. 16, 171 (2003).
4. A. Herman-Bert et al., Am. J. Hum. Genet. 67, 229 (2000).
5. P. Ghanshani et al., Genomics 12, 190 (1992).
6. S. K. Aggarwal and R. MacKinnon, Neuron 16, 1169 (1996).
7. S. M. Pulst, Ed. Genetics of Movement Disorders. Academic Press, San Diego 2002.
8. L. Schols, P. Bauer, T. Schmidt, T. Schulte, O. Riess, Lancet Neurol. 5, 291 (2004).
9. M. F. Waters et al. Neurology epub ahead of print (2005).
10. B. Rudy and C. J. McBain, Trends Neurosci. 9, 517 (2001).
11. M. Covarrubias, A. Wei, L. Salkoff, Neuron 7, 763 (1991).
12. N. V. Shen, and P. J. Pfaffinger, Neuron 14, 625 (1995).
13. S. B. Long, E. B. Campbell, R. MacKinnon, Science 309, 897 (2005).
14. C. C. Shieh, K. G. Klemic, G. E. Kirsch, J. Gen. Physiol. 109, 767 (1997).
15. C. J. Smith-Maxwell, J. L. Ledwell, R. W. Aldrich, J. Gen. Physiol. 111, 421 (1998).
16. S. A. Seoh, D. Sigg, D. M. Papazian, F. Bezanilla, Neuron 16, 1159 (1996).
17. M. Martina, G. L. Yao, B. P. Bean, J. Neurosci. 23, 5698 (2003).
18. B. E. McKay and R. W. Turner, Eur. J. Neurosci. 20, 729 (2004).
19. D. S. Goldman-Wohl, E. Chan, D. Baird, N. Heintz, J. Neurosci. 14, 511 (1994).
20. M. Weiser et al., J. Neurosci. 14, 949 (1994).
21. F. Espinosa, et al., J. Neurosci. 21, 6657 (2001).
22. 1 P. Ruppersberg et al., Nature 352, 711 (1991).
23. E. Vega-Saenz de Miera, B. Rudy, Biochem. Biophys. Res. Comm. 186, 1681 (1992).
24. F. Duprat, Proc. Natl. Acad. Sci. U.S.A. 92, 11796 (1995).
25. B. E. McKay and R. W. Turner, J. Physiol. epub ahead of print (2005).
26. C. T. Schulteis, N. Nagaya, D. M. Papazian, J. Biol. Chem. 273, 26210 (1998).

REFERENCES 27. 1 L. Rae, A. R. Shepard, Exp. Eye. Res. 70,339 (2000).
28. W. R. Silverman, C. Y. Tang, A. F. Mock, K. B. Huh, D. M. Papazian, J. Gen. Physiol. 116, 663 (2000).

The invention claimed is:

1. A method of diagnosing spinocerebellar ataxia type 13 in a human comprising detecting in a sample containing DNA from said human a mutation in a gene coding for the voltage-gated potassium channel KCNC3, wherein said mutation causes an amino acid substitution of R420H in a protein (SEQ ID NO: 17) encoded by the KCNC3 gene, wherein the presence of said mutation in said sample is indicative of spinocerebellar ataxia type 13 in said human.

2. The method of claim 1, wherein said mutation is detected by dot blot hybridization.

3. The method of claim 1, wherein said mutation is detected by southern blot hybridization.

4. The method of claim 1, wherein said mutation is detected by sequencing said amplification product.

* * * * *

SEQUENCE LISTING

<160> NUMBER OF SEQ ID NOS: 14

<210> SEQ ID NO 1
<211> LENGTH: 23
<212> TYPE: DNA
<213> ORGANISM: Artificial
<220> FEATURE:
<223> OTHER INFORMATION: Primer

<400> SEQUENCE: 1
taggtgaggg cgtgcgatct gtt                                             23

<210> SEQ ID NO 2
<211> LENGTH: 19
<212> TYPE: DNA
<213> ORGANISM: Artificial
<220> FEATURE:
<223> OTHER INFORMATION: Primer

<400> SEQUENCE: 2
gcccgcggaa ggacgagac                                                  19

<210> SEQ ID NO 3
<211> LENGTH: 22
<212> TYPE: DNA
<213> ORGANISM: Artificial
<220> FEATURE:
<223> OTHER INFORMATION: Primer

<400> SEQUENCE: 3
ctcccaccca atcccgtcgg tc                                              22

<210> SEQ ID NO 4
<211> LENGTH: 23
<212> TYPE: DNA
<213> ORGANISM: Artificial
<220> FEATURE:
<223> OTHER INFORMATION: Primer

<400> SEQUENCE: 4
gcgatgctgc cggtaggtca tcc                                             23

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
tcgcgtacgt gctcaactac ta                                              22

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
tggggaagag gcttctagga g                                               21

<210> SEQ ID NO 7
<211> LENGTH: 18

<212> TYPE: DNA
<213> ORGANISM: Artificial
<220> FEATURE:
<223> OTHER INFORMATION: Primer

<400> SEQUENCE: 7
gggcactgga agggtctt                                                 18

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
atggggatgt tcttgaagta ggt                                           23

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
cgccaccatg atttactacg c                                             21

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10 ttttctccc tcacctcttc gac                                            23

<210> SEQ ID NO 11
<211> LENGTH: 22
<212> TYPE: DNA
<213> ORGANISM: Artificial
<220> FEATURE:
<223> OTHER INFORMATION: Primer

<400> SEQUENCE: 11
atcttgcccc accgcgtgtt ca                                            22

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
cggtcagtgg gggctgcatg ttc                                           23

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13

```
gaaatgatcc cggcggcgtt tct                                         23

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ggcagcaagg cgggatggtg                                             20
```